(12) United States Patent
Endlich et al.

(10) Patent No.: US 11,155,806 B2
(45) Date of Patent: Oct. 26, 2021

(54) METHODS AND USES OF INTRODUCING MUTATIONS INTO GENETIC MATERIAL FOR GENOME ASSEMBLY

(71) Applicant: The Board of Trustees of the Leland Stanford Junior University, Stanford, CA (US)

(72) Inventors: Solomon Endlich, Stanford, CA (US); Devin King, Stanford, CA (US); Ashby J. Morrison, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/666,187

(22) Filed: Oct. 28, 2019

(65) Prior Publication Data
US 2020/0140848 A1 May 7, 2020

Related U.S. Application Data

(60) Provisional application No. 62/751,469, filed on Oct. 26, 2018.

(51) Int. Cl.
*C12N 15/10* (2006.01)
*C12Q 1/6874* (2018.01)
*C40B 20/04* (2006.01)

(52) U.S. Cl.
CPC ....... *C12N 15/102* (2013.01); *C12N 15/1031* (2013.01); *C12Q 1/6874* (2013.01)

(58) Field of Classification Search
CPC ...... C12Q 1/68; C12Q 1/6874; C12N 15/102; C12N 15/1031
See application file for complete search history.

(56) References Cited

U.S. PATENT DOCUMENTS

2007/0020639 A1* 1/2007 Shapero ........... C12Q 2525/131
435/6.11
2014/0227709 A1* 8/2014 Knapp ................ C12Q 1/6837
435/6.12

(Continued)

FOREIGN PATENT DOCUMENTS

WO 2002079502 A1 10/2002
WO WO-2019152860 A1 * 8/2019 ........... C12Q 1/6853

(Continued)

OTHER PUBLICATIONS

Thermo Fisher Scientific; The Long and Short of Isothermal Amplification; Oct. 7, 2019 (Year: 2019).*

(Continued)

*Primary Examiner* — Jeremy C Flinders
*Assistant Examiner* — Taryn Kimberly Wood
(74) *Attorney, Agent, or Firm* — KPPB LLP

(57) ABSTRACT

Methods of sequencing and assembling a nucleic acid sequence from a nucleic acid sample containing repetitive or low-information regions, which are typically difficult to sequence and/or assemble are provided. The methods of sequencing and assembling introduce mutations into the sample to increase sequence diversity between various repetitive regions present in the nucleic acid sample. This sequence diversity allows various segments to assemble independently of different, but similar sequences present in the nucleic acid sample.

13 Claims, 21 Drawing Sheets

(56) References Cited

U.S. PATENT DOCUMENTS

2016/0257984 A1*  9/2016  Hardenbol ........... C12Q 1/6806
2017/0067101 A1*  3/2017  Clarke ................ C12Q 1/6869
2017/0306392 A1* 10/2017  Wigler ................ C12Q 1/6827

FOREIGN PATENT DOCUMENTS

WO      2020087076 A1    4/2020
WO      2020087076 A8    6/2020

OTHER PUBLICATIONS

Kumar et al., "Mutational sequencing for accurate count and long-range assembly", bioRxiv, Jun. 13, 2017, 14 pgs., doi: https://doi.org/10.1101/149740.
Levy et al., "Facilitated sequence counting and assembly by template mutagenesis", PNAS, Oct. 28, 2014, First Published: Oct. 13, 2014, vol. 111, No. 43, pp. E4632-E4637, https://doi.org/10.1073/pnas.1416204111.
Zaccolo et al., "An Approach to Random Mutagenesis of DNA Using Mixtures of Triphosphate Derivatives of Nucleoside Analogues", Journal of Molecular Biology, Feb. 2, 1996, vol. 255, No. 4, pp. 589-603,https://doi.org/10.1006/jmbi.1996.0049.
International Search Report and Written Opinion for International Application No. PCT/US2019/058379, Search completed Jan. 5, 2020, dated Jan. 22, 2020, 11 Pgs.

* cited by examiner

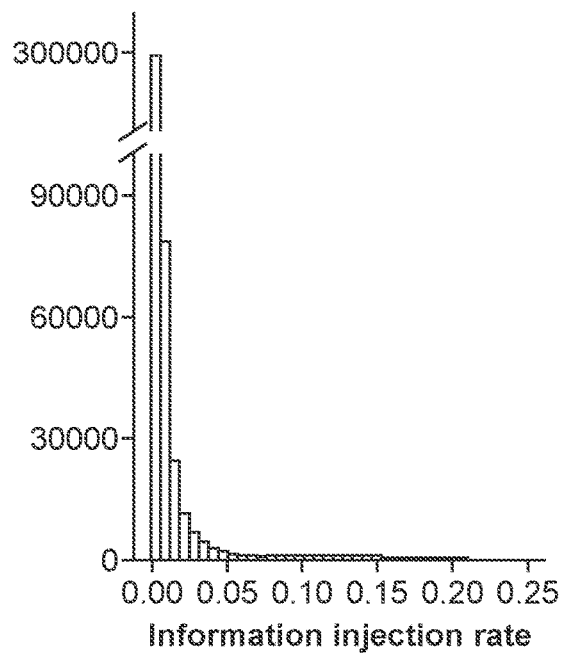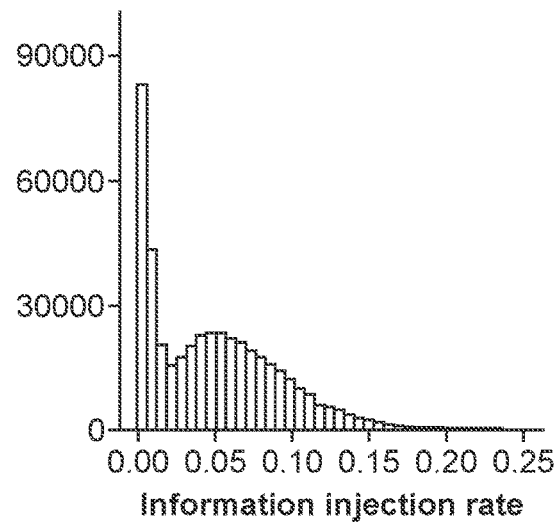
FIG. 4A    FIG. 4B
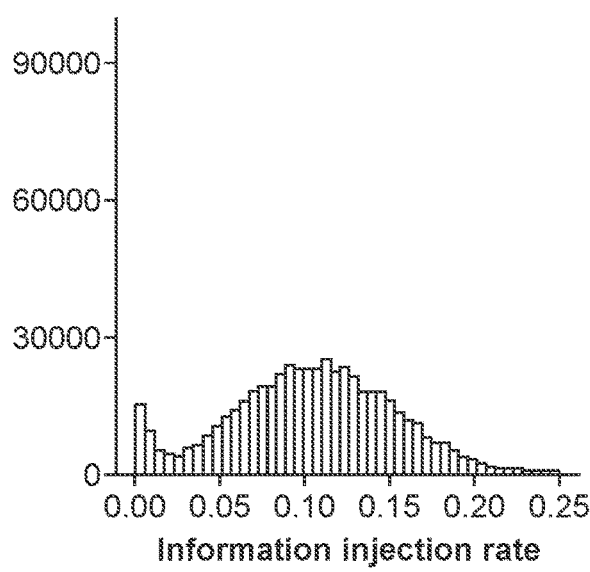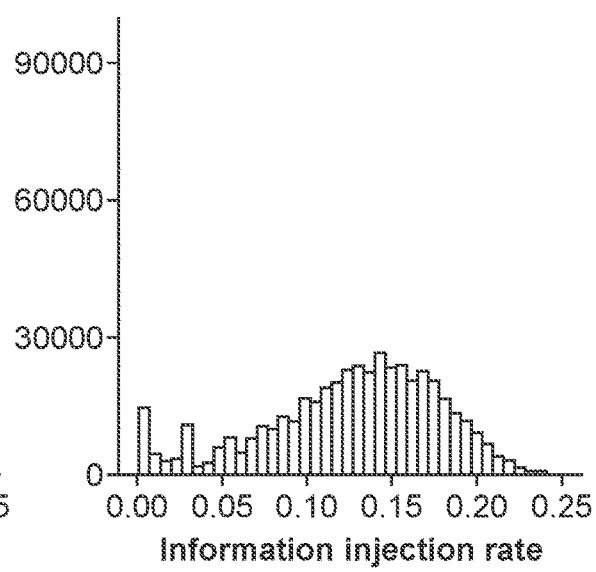
FIG. 4C    FIG. 4D

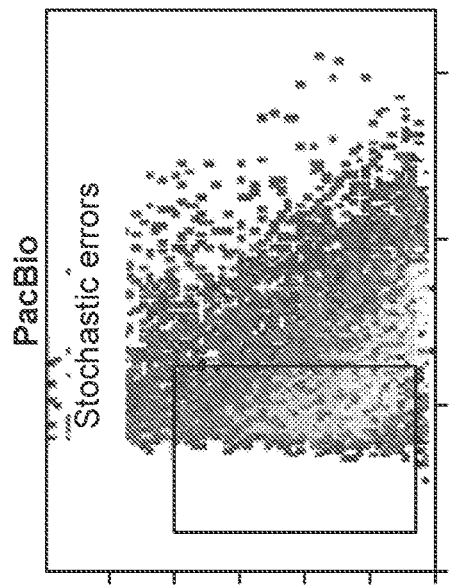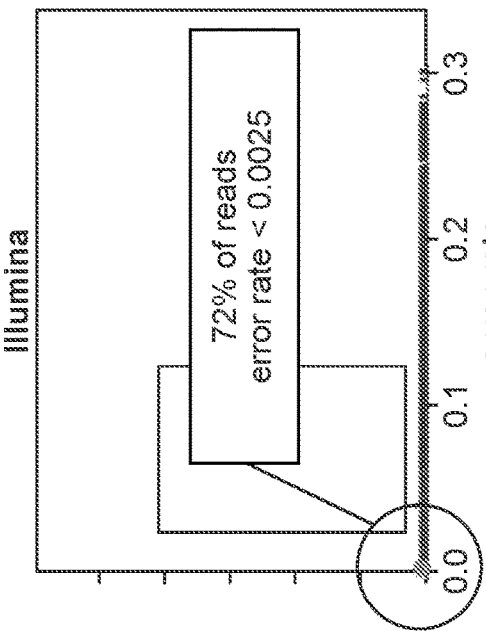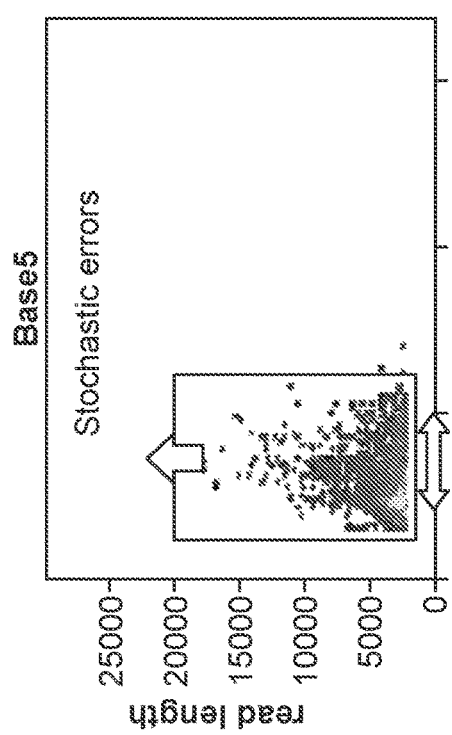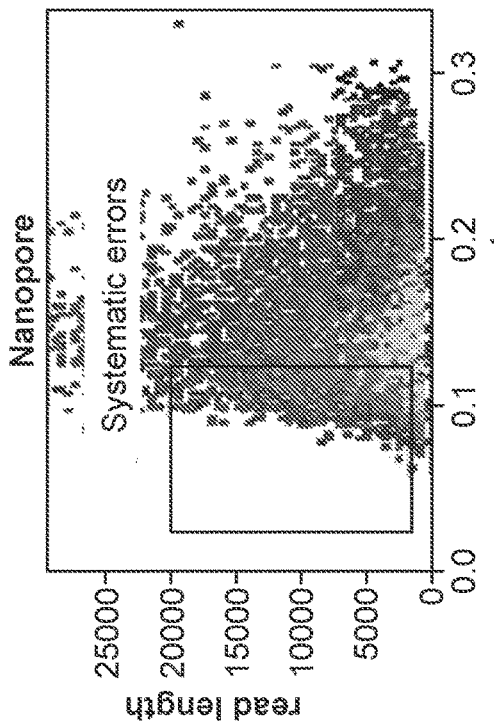
FIG. 5B
FIG. 5C
FIG. 5D
FIG. 5E

| Spades assembly | | Abyss assembly | | Embodiments | |
|---|---|---|---|---|---|
| # contigs (>= 0 bp) | 995 | # contigs (>= 0 bp) | 75 | # contigs (>= 0 bp) | 1 |
| # contigs (>= 1000 bp) | 19 | # contigs (>= 1000 bp) | 28 | # contigs (>= 1000 bp) | 1 |
| # contigs (>= 5000 bp) | 7 | # contigs (>= 5000 bp) | 10 | # contigs (>= 5000 bp) | 1 |
| # contigs (>= 10000 bp) | 3 | # contigs (>= 10000 bp) | 2 | # contigs (>= 10000 bp) | 1 |
| # contigs (>= 25000 bp) | 1 | # contigs (>= 25000 bp) | 1 | # contigs (>= 25000 bp) | 1 |
| # contigs (>= 50000 bp) | 1 | # contigs (>= 50000 bp) | 0 | # contigs (>= 50000 bp) | 1 |
| Total length (>= 0 bp) | 428403 | Total length (>= 0 bp) | 156962 | Total length (>= 0 bp) | 164666 |
| Total length (>= 1000 bp) | 154363 | Total length (>= 1000 bp) | 144800 | Total length (>= 1000 bp) | 164666 |
| Total length (>= 5000 bp) | 123780 | Total length (>= 5000 bp) | 95461 | Total length (>= 5000 bp) | 164666 |
| Total length (>= 10000 bp) | 96475 | Total length (>= 10000 bp) | 46280 | Total length (>= 10000 bp) | 164666 |
| Total length (>= 25000 bp) | 54329 | Total length (>= 25000 bp) | 35109 | Total length (>= 25000 bp) | 164666 |
| Total length (>= 50000 bp) | 54329 | Total length (>= 50000 bp) | 0 | Total length (>= 50000 bp) | 164666 |
| # contigs | 44 | # contigs | 33 | # contigs | 1 |
| Largest contig | 54329 | Largest contig | 35109 | Largest contig | 164666 |
| Total length | 170335 | Total length | 148418 | Total length | 164666 |
| GC (%) | 44.24 | GC (%) | 43.81 | GC (%) | 43.92 |
| # N's per 100kbp | 0.00 | # N's per 100kbp | 0.67 | # N's per 100kbp | 0.00 |

FIG. 7A

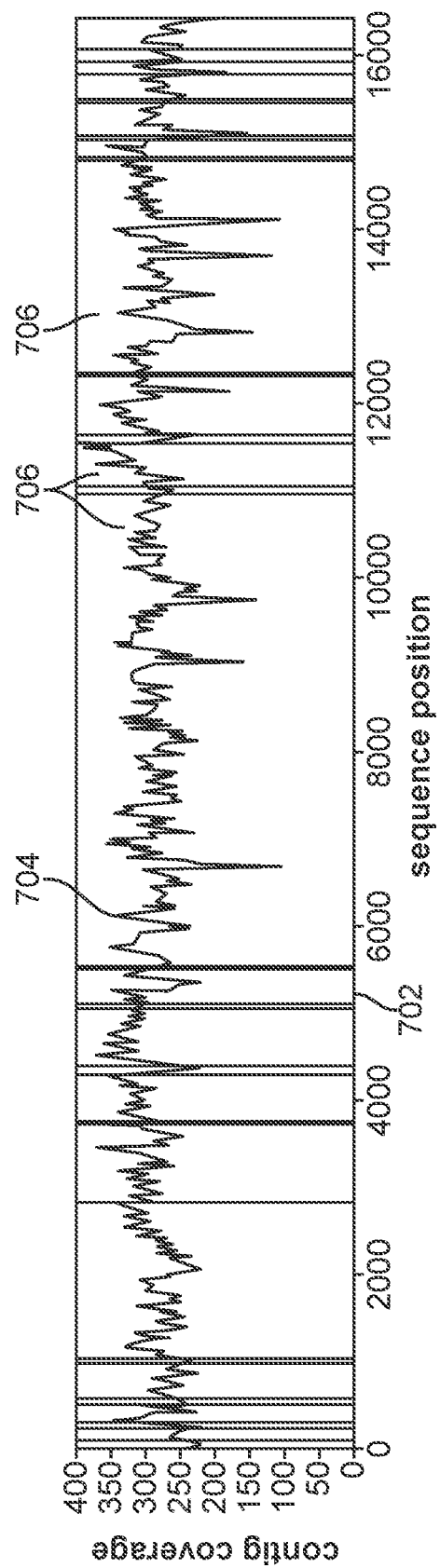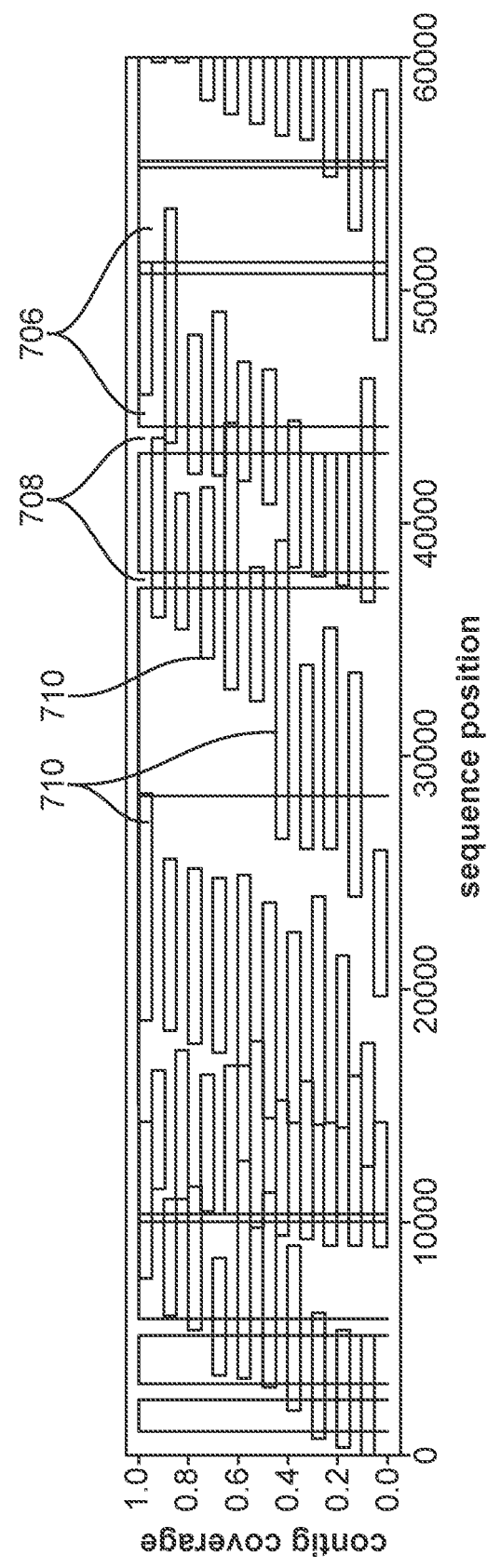
FIG. 7B
FIG. 7C

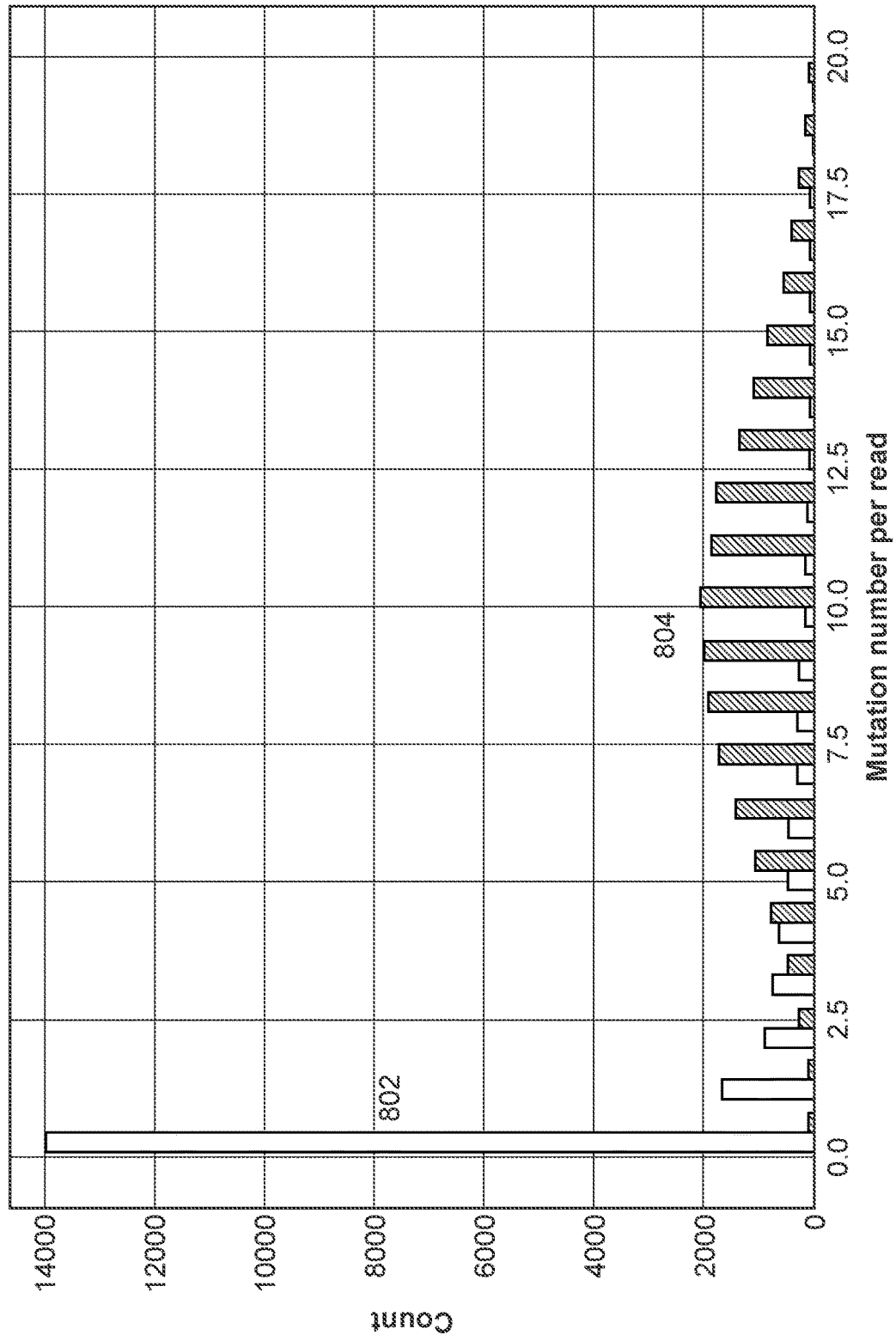

METHODS AND USES OF INTRODUCING MUTATIONS INTO GENETIC MATERIAL FOR GENOME ASSEMBLY

CROSS REFERENCE TO RELATED APPLICATIONS

The current application claims priority to U.S. Provisional Patent Application No. 62/751,469 entitled "Methods and Uses of Introducing Mutations into Genetic Material for Genome Assembly" to Endlich et al., filed Oct. 26, 2018, the disclosure of which is hereby incorporated by reference in its entirety.

FIELD OF THE INVENTION

The present invention is directed to nucleic acid sequencing, including methods and applications thereof, more particularly, genome sequencing of organisms, including organisms possessing complex genomes that are traditionally difficult to sequence and assemble. The present invention is also directed to methods of assembling genomic sequences derived from complex genomes.

BACKGROUND OF THE INVENTION

The cost of nucleic acid sequencing has decreased dramatically as sequencing and data analysis technologies have improved. This cost reduction has made individualized or personalized medicine based on a person's own genetic sequence attainable. However, typical biological sequences (such a genome sequences) can have repetitive and low information regions that make assembly a much more difficult and often an impossible task. In large Eukaryotic genomes, such as human and plant genomes, these problems can be especially severe and make the assembly of these genomes (or genomic subregions) a much more difficult task compared to smaller, more information rich genomes, such as *Escherichia coli*. The most obvious way to combat these difficulties is to increase read length. Unfortunately, contemporary sequencing platforms capable of long reads are accompanied by very high error rates (as compared to short-read platforms), in addition to limiting sample requirements, such as large amounts of input DNA. Thus, alternative methods to allow genome sequencing and assembly across repetitive regions and low-information regions will improve genome assembly.

SUMMARY OF THE INVENTION

Methods and uses of introducing mutations into genetic material for genome sequencing and assembly are disclosed.

In one embodiment, a method of assembling a genome sequence includes obtaining a nucleic acid sample, mutating the nucleic acid sample, sequencing the mutated nucleic acid sample, and assembling the sequenced mutated nucleic acid sample to build a genome sequence.

In a further embodiment, the method further includes performing size selection on the nucleic acid sample to select a desired size of fragments and generating a sequencing library for the size selected nucleic acid sample, and the mutating step is accomplished by performing a mutagenic reaction on the nucleic acid sample.

In another embodiment, the method further includes the steps of quantifying the size selected nucleic acid sample, and changing the concentration of the size selected nucleic acid sample to a desired concentration.

In a still further embodiment, the changing of the concentration step comprises diluting the size selected nucleic acid sample.

In still another embodiment, the method further includes the step of amplifying the size selected nucleic acid sample to generate additional copies of the size selected nucleic acid sample.

In a yet further embodiment, the amplifying step uses a multiple strand displacement amplification reaction.

In yet another embodiment, the amplifying step uses approximately 0.5-10 ng of input nucleic acid.

In a further embodiment again, the introducing mutations step of the method includes performing a multiple displacement amplification reaction using a nucleotide analog.

In another embodiment again, the multiple strand displacement amplification reaction uses Phi29 DNA polymerase.

In a further additional embodiment, the nucleotide analog is selected from the group consisting of deoxy-inosine triphosphate, deoxy-8-oxoguanine triphosphate, and deoxy-2'-Deoxy-P-nucleoside triphosphate.

In another additional embodiment, the nucleotide analog is deoxy-2'-Deoxy-P-nucleoside triphosphate.

In a still yet further embodiment, the generating a sequencing library step generates a sequencing library for an Illumina sequencing platform, and the sequencing step uses an Illumina sequencing platform to sequence the nucleic acid sample.

In still yet another embodiment, a method for producing a sequencing library includes obtaining a template nucleic acid, introducing mutations into the template nucleic acid to create a mutated sample, and generating a sequencing library from the mutated sample.

In a still further embodiment again, the mutations are introduced via a multiple strand displacement amplification.

In still another embodiment again, the multiple strand displacement amplification incorporates a nucleotide analog during the amplification.

In a still further additional embodiment, the nucleotide analog is selected from the group consisting of deoxy-inosine triphosphate, deoxy-8-oxoguanine triphosphate, and deoxy-2'-Deoxy-P-nucleoside triphosphate.

In still another additional embodiment, the multiple strand displacement amplification uses Phi29 DNA polymerase and the nucleotide analog is deoxy-2'-Deoxy-P-nucleoside triphosphate.

In a yet further embodiment again, the mutations are introduced using a chemical mutagen.

In yet another embodiment again, the method further includes amplifying the mutated sample and the sequencing library is generated from the amplified mutated sample.

In a yet further additional embodiment, the method further includes size selecting the mutated sample and quantifying the size selected mutated sample.

BRIEF DESCRIPTION OF THE DRAWINGS

These and other features and advantages of the present invention will be better understood by reference to the following detailed description when considered in conjunction with the accompanying drawings where:

FIGS. 4A-4D illustrate mismatch rate of sequencing reads from mutated and non-mutated sequencing reads in accordance with embodiments of the invention.

FIG. 5B illustrates contig size and mismatch rate after assembly of mutated sequencing reads in accordance with embodiments of the invention.

FIGS. 5C-5E illustrate read length and error rate of sequencing reads from other technologies in accordance with embodiments of the invention.

FIG. 7A illustrates a table summarizing assembly statistics of a repetitive bacterial artificial chromosome in accordance with embodiments of the invention.

FIGS. 7B-7C illustrates the assembly and alignment of sequencing reads and contig assemblies of a repetitive bacterial artificial chromosome in accordance with embodiments of the invention.

FIG. 8 illustrates the number of mismatches in 98 bp reads in mutated and control samples against the *Arabidopsis thaliana* reference genome in accordance with embodiments of the invention.

DETAILED DISCLOSURE OF THE INVENTION

Turning now to the diagrams and figures, embodiments of the invention are generally directed to genome sequencing and assembly in accordance with many embodiments of the invention are illustrated. In various embodiments, mutations are introduced into isolated DNA. In some embodiments, the introduced mutations create differences in the isolated DNA that create unique templates in the isolated DNA. In certain embodiments, the unique templates allow for the assembly of repetitive regions. In some embodiments, the mutated template is created using a nucleotide analog incorporated into replicated DNA. In some such embodiments, the nucleotide analog is dPTP.

Current genome sequencing typically use "shotgun" sequencing, where small segments of nucleic acids (typically 100-200 base pairs each) are sequenced and assembled into larger sequences based on sequence similarity between each segment. However, many genomes contain large, repetitive regions throughout the genome. Sequence similarity in these repetitive regions is very high, and the small length of the smaller segments is not enough to span many of these repetitive regions. As such, many of the smaller segments assemble to sequences that are similar, but may not be in the proper location of the genome. This mis-assembly can result in large gaps in an assembled genome. Additionally, some of these regions are difficult to sequence based on inherent biases in current sequencing platforms. Since sequencing these regions is not always possible, a full, definitive assembly cannot be built, which will result in additional gaps in an assembled genome. Because of these gaps, assembled genomes are missing key pieces of information about the structure of a genome, including structural abnormalities, including insertions, deletions, and translocations, as well physical distances between certain regions, including distances between genes and elements capable of regulating the gene, such as a promoter, an enhancer, an insulator, or other regulatory region. Some genetic diseases are linked to structural variation, thus it is important to unlock the knowledge and information that is contained in the regions that are difficult to sequence and/or assemble.

Some current methodologies to sequence across these regions include using long-range sequencing, such as the PacBio platform, which can generate longer sequencing reads. However, these platforms possess large error rates, which reduce accuracy result and can result in a poor quality genome assembly. Additionally, these platforms require large quantities of input nucleic acids (e.g., DNA) in order to build sequencing libraries. Thus, to assemble a genome, fully and accurately, new methods must be developed, which overcome the difficulties in the genome itself and biases in sequencing platforms.

Figure 1:
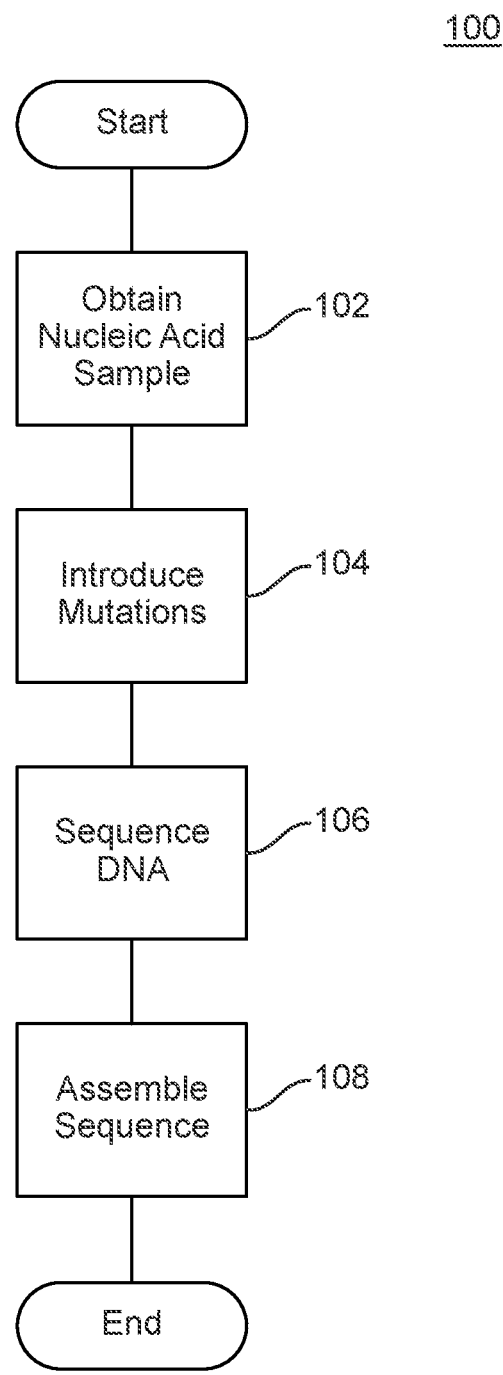
FIG. 1 illustrates a method to sequence and assemble a genome sequence in accordance with embodiments of the invention.

Embodiments of the present invention overcome these challenges by introducing random mutations into a nucleic acid sample to increase sequence diversity between regions that show high levels of sequence similarity. By doing so, the mutated sequences are readable by a nucleic acid sequencer and can be assembled using sequence assembly software. Embodiments disclosed herein demonstrate techniques to insert stochastic mutations at a tunable rate, which is large enough that difficult-to-assemble regions can now be assembled. FIG. 1 illustrates a process 100 in accordance with various embodiments to sequence and assemble a genome or complex genomic region of a subject.

In process 100, an initial step is to obtain a nucleic acid sample 102. In embodiments, the nucleic acid sample is deoxyribonucleic acid (DNA), while in other embodiments, the nucleic acid sample is ribonucleic acid (RNA). In embodiments, the nucleic acid sample is genomic DNA, while other embodiments will obtain a smaller fragment of DNA, such as a plastid DNA, mitochondrial DNA, or DNA isolated in the form of a plasmid, a fosmid, a cosmid, a bacterial artificial chromosome (BAC), a yeast artificial chromosome (YAC), and/or any other sub-genome segment of DNA.

Additionally, at step 102, the DNA may be obtained in any number of ways. In certain embodiments, DNA will be obtained from amplifying DNA present in an environment without an isolation step, while certain embodiments will enrich specific sequences (e.g., targeted enrichment). In certain embodiments, the DNA is isolated from an entire organism or a subpart of an organism, such as an organ or tissue. Isolated DNA can be obtained in any suitable method to isolate DNA, such as using a published protocol or a commercial DNA isolation kit. In some embodiments, the DNA may already be isolated, and the obtaining DNA step 102 is merely to select or remove a portion of the DNA sample for further use in the process 100.

At step 104, mutations are introduced into the DNA obtained in step 102. At this step, the DNA is mutated to increase sequence differences in the obtained DNA. Mutations may be introduced by any number of ways, such as chemical mutagens, ionizing mutagens, or biochemical mutagens At step 106, the mutated nucleic acid is sequenced in some embodiments. At sequencing step 106, sequencing can occur via map-based sequencing, such that sequence is read in an organized fashion, or sequencing at step 106 can occur via shotgun sequencing, where sequencing occurs to a large number of fragments, then assembled at a later step (e.g., step 108, described below). Sequencing at step 106 can be to any suitable depth for genome assembly, such that some embodiments will sequence to a depth of approximately 1x, where x is the size of the template or reference nucleic acid. In some embodiments, a greater depth may be necessary to fully assemble the sequence. Thus, various embodiments will sequence the sample to a depth of approximately 2x, approximately 3x, approximately 4x, approximately 5x, approximately 10x, approximately 15x, approximately 20x, approximately 25x, approximately 30x, approximately 40x, approximately 50x, or approximately 100x.

Specific machinery used at sequencing step 106 can be performed on any suitable sequencing platform or platforms suitable for further assembly. In some embodiments, sequencing is performed on a suitable sequencing platform, such as an ABI 3730, an ABI SOLiD, an Illumina HiSeq, an Illumina MiSeq, an Illumina MiniSeq, an Illumina iSeq, an Illumina NexSeq, an Illumina NovSeq, an MGISEC-T7, a Roche 454, an Ion Torrent PGM, an Ion Torrent Proton, a Helicos platform, a Pacific Biosciences RSII, a Pacific Biosciences Sequel, an Oxford Nanopore MinION, an Oxford Nanopore GridION, an Oxford Nanopore PromethION, and/or a combination thereof. To sequence the mutated nucleic acid, various embodiments will generate a sequencing library suitable for the sequencing platform or platforms performing the sequencing. In some embodiments, the sequencing library will be built for single-end sequencing, while certain embodiments will build a library for paired-end sequencing, and various embodiments will build a library for mate-pair sequencing.

Further, process 100 assembles the nucleic acid sequence at step 108. In some embodiments, assembly is performed as a single step with the entire reference being assembled at once, while other embodiments will perform multiple rounds of assembly to allow for fragments to assemble, which are then assembled into a full reference sequence.

At step 108, assembly can use one or more algorithms or software packages for assembly suitable to the needs of the genome, such as short read sequencing (e.g., 100-300 base reads) or long read sequencing (10,000+ base reads). For example, various embodiments will use AFEAP cloning Lasergene Genomics Suite, DNASTAR Lasergene Genomics Suite, Newbler, Phrap, Plass, SPAdes, Velvet, HGAP, Falcon, Canu, MaSuRCA, Hinge, ABySS, Bowtie, and/or a combination thereof, which are suitable for read length or fragment size. In embodiments where short reads are assembled into larger sequences before a full assembly, a combination of a short-read assembler is used to assemble short reads into larger fragments followed by a long-read assembler to assemble the larger fragments into a full reference sequence. In some embodiments using a combination of short- and long-read assemblers, these embodiments will use at least one of ABySS and SPAdes for short-read assembly and Canu for long read assembly.

While process 100 generally describes the process of various embodiments disclosed herein, certain embodiments will include additional, specific steps as part of some of the steps described above, which are described in depth below.

Additionally, the above steps of the flow diagram of FIG. 1 may be performed in a different order or sequence and is not limited to the order or sequence shown and described in the figures. Some of the above steps of the flow diagram of FIG. 1 may be executed or performed substantially simultaneously where appropriate or in parallel to reduce delay, cost, or other expense. Some of the above steps of the flow diagram of FIG. 1 may be omitted or performed additional times as desired or necessary to acquire specific characteristics of the process, including, for example, performing multiple sequencing and assembly steps.

Introduction of Mutations into Sample

Figure 2:
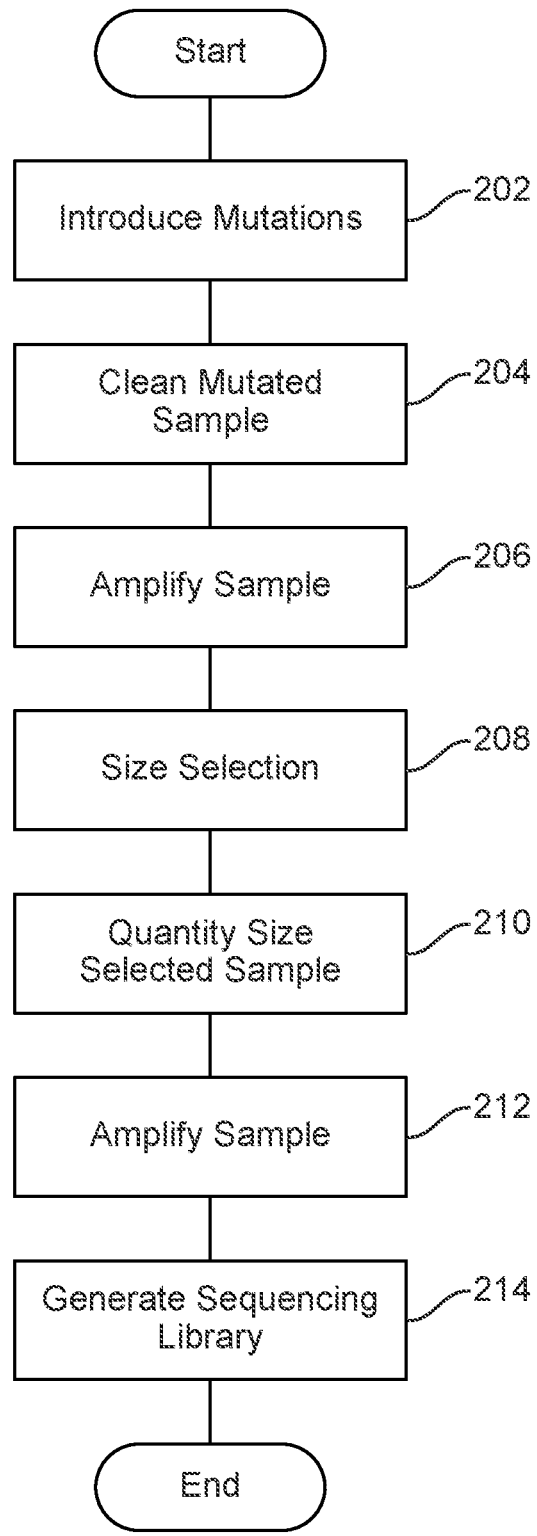
FIG. 2 illustrates a method to mutate a nucleic acid sample in preparation to sequence in accordance with embodiments of the invention.

Turning now to FIG. 2, a process 200 of introducing mutations into the sample is described. At Step 202, various embodiments will introduce mutations into a nucleic acid sample. As noted above in reference to FIG. 1, mutations may be introduced by any number of ways, such as chemical mutagens, ionizing radiation, or biochemical means to introduce mutations. A desirable mutation rate is a rate which creates enough sequence diversity between similar repetitive regions to allow assembly of one region independent of other regions. Many embodiments will allow for the tuning of the mutation rate, means of tuning the mutation rate are described further herein.

In embodiments utilizing chemical mutagenesis, the nucleic acid sample is exposed to a chemical mutagen, which alters a base and/or an interaction between bases, which allow for a different base to be introduced into the nucleic acid. Various embodiments will use ethyleneimine (EI), nitrogen mustard, Sulphur mustard, sodium bisulfite, diethylnitrosamine (DMN), diethylsulphonate (DES), nitrosomethylurea (NMU), ethyleneoxide (EO), diepoxybutane (DEB), diethylsulphonate (DES), methylmethanesulphonate (MMS), ethylmethanesulphonate (EMS), nitrous acid, maleic hydrazide, hydroxylamine, and/or combinations thereof to alter the nucleic acid. In various embodiments, alternate bases are introduced during replication of the sample nucleic acid, based on the alteration caused by one or more of the above mutagens.

Similar to chemical mutagenesis, certain embodiments will use ionizing radiation to alter bases and/or base interactions. Various embodiments will expose the nucleic acid sample to radiation, such as UV radiation, gamma radiation, alpha particles, beta particles, and/or combinations thereof to create base pair changes in the nucleic acid sample. As noted above, alternate bases are introduced during replication of the sample nucleic acid, based on the alteration caused by one or more of the above ionizing radiation methods.

Further, some embodiments will utilize biochemical mutagenesis, which utilizes DNA replication machinery, such as a polymerase, to introduce mutations. In certain embodiments, an error-prone polymerase will be used to introduce base pair mismatches. Additional embodiments will utilize nucleotide analogs to substitute for bases during replication, which allow for different bases to be introduced during replication of the sample nucleic acid, thus creating a mutated version of the sample nucleic acid. These biochemical methods can utilize techniques, such as polymerase chain reaction (PCR), multiple strand displacement amplification (MDA) methods, rolling circle amplification (RCA), and any other known method of amplifying and/or replicating nucleic acids in vitro. Because certain embodiments will introduce mutations using amplification and/or replication reactions, a smaller amount of input nucleic acid can be utilized as compared to long-read methodologies. As such, a number of embodiments will use approximately nanogram levels of input nucleic acid, rather than the microgram starting amounts of nucleic acid in long-read platforms. For example, several embodiments will use approximately 0.5-10 ng of starting nucleic acid, while additional embodiments will use less than 0.5 ng of starting nucleic acid.

Various embodiments will use 5-fluoro uracil, 5-iodo deoxyuridine, 6-mercaptopurine, 6-thioguanine, 8-azaguanine, 5-azauridine, 6-azauridine, 6-azacytidine, 4-hydroxypyrazolopyrimidine, inosine, 8-oxoguanine, 2'-Deoxy-P-nucleoside, and/or combinations thereof. When using a nucleotide analog, the above bases will be attached to a ribose-triphosphate or deoxyribose-triphosphate in order to be incorporated into a new strand during the polymerization of RNA or DNA, respectively.

Figure 3:
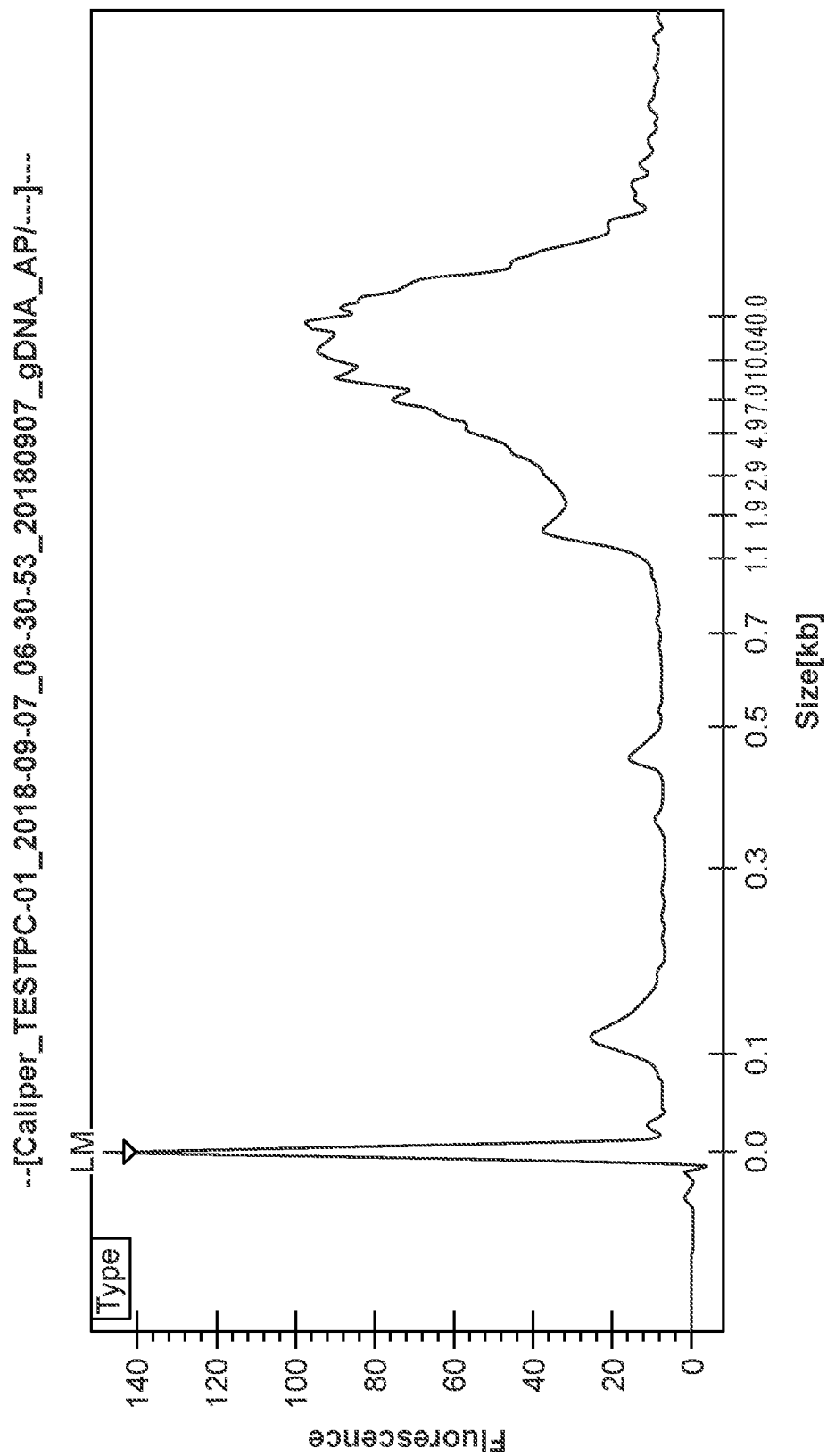
FIG. 3 illustrates an electropherogram of isolated fragments after multiple displacement amplification (MDA) in accordance with embodiments of the invention.

In embodiments using a polymerase to introduce mutations, the polymerase is a standard polymerase used for molecular replication, such as DNA polymerase I, DNA polymerase II, DNA polymerase III, DNA polymerase IV, DNA polymerase V, RNA polymerase I, RNA polymerase II, RNA polymerase III, RNA polymerase IV, RNA polymerase V, Taq polymerase, Phi29 polymerase, Bst polymerase, Bsu DNA polymerase, Vent exo-DNA polymerase, T4 DNA polymerase, T7 DNA polymerase, T7 RNA polymerase, any other applicable polymerase, enzymatic variants of polymerases (e.g., EquiPhi29), and/or a combination thereof. In some embodiments, the polymerase is selected for processivity, such that polymerases that have high levels of processivity can be beneficial for generating long segments of replicated DNA and/or RNA. In additional embodiments, the polymerase can be selected for exonuclease activity. Exonuclease activity is typically associated with error correcting in strand replication, such that a base pair mismatch is excised from the replicated strand and polymerization continues. As such, various embodiments will select polymerases exhibiting reduced exonuclease activity. Further, various embodiments will select a polymerase for strand displacement properties, which allow the polymerase to displace a complementary segment of DNA or RNA that is bound to a template or reference segment of DNA or RNA. Strand displacement properties allow for a polymerase to continually polymerize a growing strand of DNA despite any prior existing pieces of DNA or RNA. As such, polymerases exhibiting strand displacement properties may allow for longer pieces of replicated DNA or RNA to be generated. In many embodiments, Phi29 DNA polymerase is used as the polymerase to introduce mutations, because Phi29 DNA polymerase exhibits strand displacement properties and a high level of processivity. Although Phi29 DNA polymerase can be a good option, any DNA polymerase exhibiting similar characteristics may also be used. FIG. 3 illustrates an electropherogram of fragments generated via MDA that incorporates mutations.

t should be noted that a suitable polymerase may not possess all beneficial characteristics, such as high processivity, strand displacement, and low exonuclease activity. In situations such as this, various embodiments will select a nucleotide analog that is not susceptible to exonuclease activity of the selected polymerase. For example, certain embodiments will utilize Phi29 DNA polymerase along with 2'-Deoxy-P-nucleoside-5'-Triphosphate (dPTP). It should be noted that this combination of Phi29 DNA polymerase and dPTP is only one example of a possible polymerase and nucleotide analog within the scope of this disclosure and is not limiting on the scope of this disclosure.

Additionally, certain enzymes may not represent all regions of a genome, due to biases against GC-rich regions, due to stronger bonding between the GC base pairs. As such, alterations to amplification protocols, including amplification at higher temperatures, enzymes that do not show an anti-GC bias, a change in primer mixture and concentration, and/or a combination thereof can be used to assure amplification and sequencing of these regions. An example of higher temperature enzymes is the EquiPhi29 enzyme. Additionally, MDA generally has a bias against the ends of linear DNA fragments, causing an underrepresentation of these regions. Certain embodiments will incorporate non-random primers that increase the amplification of fragment ends to increase the read depth and assembly of these regions. Additionally, using non-random primers in some embodiments will allow for targeted sequencing of specific regions, genes, and/or other panel of interest in a target species.

Some embodiments will clean or purify the mutated sample at step 204. In embodiments including this step, the mutated nucleic acid sample is isolated from other components that persist from step 202. As such, remnant mutagens, nucleotides, enzymes, buffer, salt and/or other remnants will be removed through known means, such as using column purification, gel purification, alcohol precipitation, salt precipitation, and/or a combination thereof. Additionally, non-mutated template DNA may coprecipitate with the mutated DNA during purification. As such, this non-mutated template can be a contaminant for downstream sequencing and assembly. Certain embodiments will utilize selective methods to filter out the non-mutated template. Such selective methods include incorporating a tag or other moiety onto certain nucleotides during amplification. Such that a selection column will hold the tag or other moiety, thus allowing the non-mutated template to flow through into waste. The selection column would then allow for the elution of the mutated amplification product.

In certain embodiments, the purified sample will be quantified and diluted to a desired concentration for further use. In embodiments that quantify the sample, known methods of quantifying nucleic acids will be utilized, such as light absorption, fluorescence using a dye that binds to nucleic acids. For example, when quantifying a nucleic acid sample using absorption, a spectrophotometer capable of measuring absorption in the UV-Vis range of light is used, including spectrophotometers such as a ThermoScientific NanoDrop 2000. When using fluorescence, a suitable dye is used to bind the nucleic acid, which is then excited, and the emission wavelength is measured using a fluorometer, such as a ThermoScientific NanoDrop 3300 or Qubit. Suitable dyes will also be able to be excited by the specific fluorometer and the fluorometer will be able to read the specific emission wavelength. In various embodiments, the suitable dye is selected from ethidium bromide, propidium iodide, crystal violet, 4',6-diamidino-2-phenylindole (DAPI), 7-aminoactinomycin D (7-AAD), Hoechst 33258, Hoechst 33342, Hoechst 34580, PicoGreen, Helixyte, YOYO-1, DiYO-1, TOTO-1, DiTO-1, and/or SYBR. It should be noted that additional spectrophotometers, fluorometers, and dyes are known in the art, which are suitable for quantification of nucleic acids.

As noted above, various embodiments will dilute the mutated sample to a desired concentration. In embodiments that dilute the sample, an amount of water, buffer, or other diluent is added to bring the sample to a final concentration. Typical dilution follows formula (1):

$$C_i V_i = C_f V_f \qquad (1)$$

Where $C_i$ represents initial concentration, $V_i$ represents initial volume, $C_f$ represents final (or desired) concentration, and $V_f$ represents final volume. Following this formula, the volume of the diluent is calculated to decrease the concentration to the desired concentration.

At step 206, some embodiments will perform a clean amplification. The purpose of a clean amplification is to convert any mutated or non-canonical bases with canonical bases (e.g., cytosine, guanine, thymine, and adenine). For example, embodiments incorporating nucleotide analogs, a clean amplification will replace the analog with a canonical base. This clean amplification step can be performed in accordance with a relevant amplification method, such as those described in step 202, with the exception that any amplification reaction will add only the canonical bases without the inclusion of base analogs or other mutagens.

At step 208, various embodiments will select fragments for a specific size. In some embodiments, size selection allows the isolation of fragments of a specific size, which can be assembled prior to a full assembly of the reference sequence. The specific size used for this step can vary depending on the amount and size of repetitive regions. As such, large fragments may be necessary for genomes or other samples with large repetitive regions prior to a full assembly, while genomes or samples with smaller repetitive regions may be able to be assembled with relatively smaller fragments. As such, in some embodiments, size selection will select for fragments in the range of approximately 5,000 base pairs to approximately 10,000 base pairs, while other embodiments will select for fragments in the range of approximately 10,000 base pairs to approximately 20,000 base pairs. In further embodiments, fragments will be selected in the range of approximately 20,000 base pairs to approximately 30,000 base pairs. Additionally, in yet other embodiments, fragments will be selected in the range of approximately 30,000 base pairs to approximately 50,000 base pairs. Even more embodiments, fragments will be selected in the range of approximately 50,000 base pairs to approximately 100,000 base pairs. Certain embodiments will size select for more than one size range, e.g., these embodiments can select for fragments in the approximately 20,000 to 30,000 base pair range as well as the approximately 50,000 to 100,000 base pair range.

The specific method to select for fragments of a specific size range can vary based on the limitations of the method. In various embodiments, size selection will utilize gel electrophoresis, such as using an agarose gel or an acrylamide gel. In embodiments using gel electrophoresis, the mutated sample is electrophoresed through the gel to allow separation of fragments based on size, where smaller fragments will travel further through the gel than larger fragments. When selecting a specific size, a piece of the gel representing the desired size range will be removed, and the nucleic acid sample will be isolated from the gel through any suitable means known in the art, including using commercial gel extraction kits, Beta-Agarose I digestion, and/or a freeze-n-squeeze method. Additional methods of performing size selection are known in the art, which can be used. As such, some embodiments will utilize a bead or column capture technique, which are commercially available as kits or can be generated in a lab. Additional embodiments will use specialized machinery, such as a Sage Science Pippin Prep to size select fragments of the desired size.

At step 210, various embodiments will quantify the size-selected sample. Additional embodiments will also dilute the size-selected sample to a desired concentration. Means for performing both of these processes are known in the art and discussed above in regard to step 204.

At step 212, the size-selected sample is amplified to increase the concentration of the sample in a number of embodiments. At this step in certain embodiments, the mutated or analog bases create sequence diversity by being replaced with native bases, such as adenine, guanine, thymine, and cytosine. Methods to amplify the sample are known in the art and includes such methods as polymerase chain reaction (PCR) or multiple displacement amplification (MDA). After amplification, various embodiments will clean or purify the sample to remove remnants of the reaction. Means for cleaning or purifying the sample are discussed above in regard to step 204. Further embodiments will also quantify and/or dilute the sample place the sample at a desired concentration for further use. Methods for quantifying and diluting nucleic acid samples are discussed above in regard to step 204.

Further, various embodiments will generate a sequencing library at step 212. Numerous methods are known in the art to generate a sequencing library. Sequencing libraries are typically specific to a single sequencing platform, such that specific features or adapters are necessary on sequencing fragments in order for a sequencer to produce a sequence from a fragment. Various embodiments will utilize commercial kits to generate libraries while other embodiments will utilize known techniques to generate the sequencing libraries using protocols to introduce adapters or primers to fragments through PCR or ligation.

In certain embodiments, sequencing libraries include specific tags or barcodes to identify specific samples. In this way, some embodiments that size select fragments can utilize different barcodes for individual fragments within a single sequencing reaction. By differentially barcoding individual fragments, these embodiments can further isolate fragments to assure assembly of unique fragments in the genome.

Additionally, the above steps of the flow diagram of FIG. 2 may be performed in a different order or sequence and is not limited to the order or sequence shown and described in FIG. 2. Some of the above steps of the flow diagram of FIG. 2 may be executed or performed substantially simultaneously where appropriate or in parallel to reduce delay, cost, or other expense. Some of the above steps of the flow diagram of FIG. 2 may be omitted or performed additional times as desired or necessary to acquire specific characteristics of the process, including, for example, performing multiple cleaning, size selection, and amplifying steps.

Tuning a Mutation Rate

The ability of some embodiments to select a specific mutation rate can be accomplished in a number of ways. For example, in chemical mutagenesis, buffer concentration, mutagen concentration, reaction temperature, reaction time, adding additional reagents, template DNA concentration, and/or a combination thereof can be adjusted. By increasing or decreasing these parameters, the mutation rate can be resolved and or identified. For example, increasing mutagen concentration may increase the likelihood of mutations, thus increasing mutation rate.

In biochemical mutagenesis, the reaction parameters may also be adjusted, such that reaction temperature, adding additional reagents, base analog concentration, DNA concentration, canonical nucleotide concentration, and/or a combination thereof can be adjusted in many embodiments.

Turning to FIGS. 4A-4D, histograms of average mutations per read are illustrated, as identified by aligning reads against a reference genome. These figures illustrate that embodiments are able to generate a tunable mutation rate. In particular, FIG. 4A illustrates a non-mutated sample, while FIGS. 4B-4D illustrate samples mutated to ~5%, ~10%, and ~15% mutation rates in accordance with many embodiments. While this figure shows mutation rates of approximately 5%, 10%, and 15%, it will be understood that the methods to tune the mutation rate can be used to customize a wide range of mutation rates, including rates greater than 15% (e.g., ~20%, ~25%, ~30%, or greater).

Assembly of Mutated Fragments

Figure 5A:
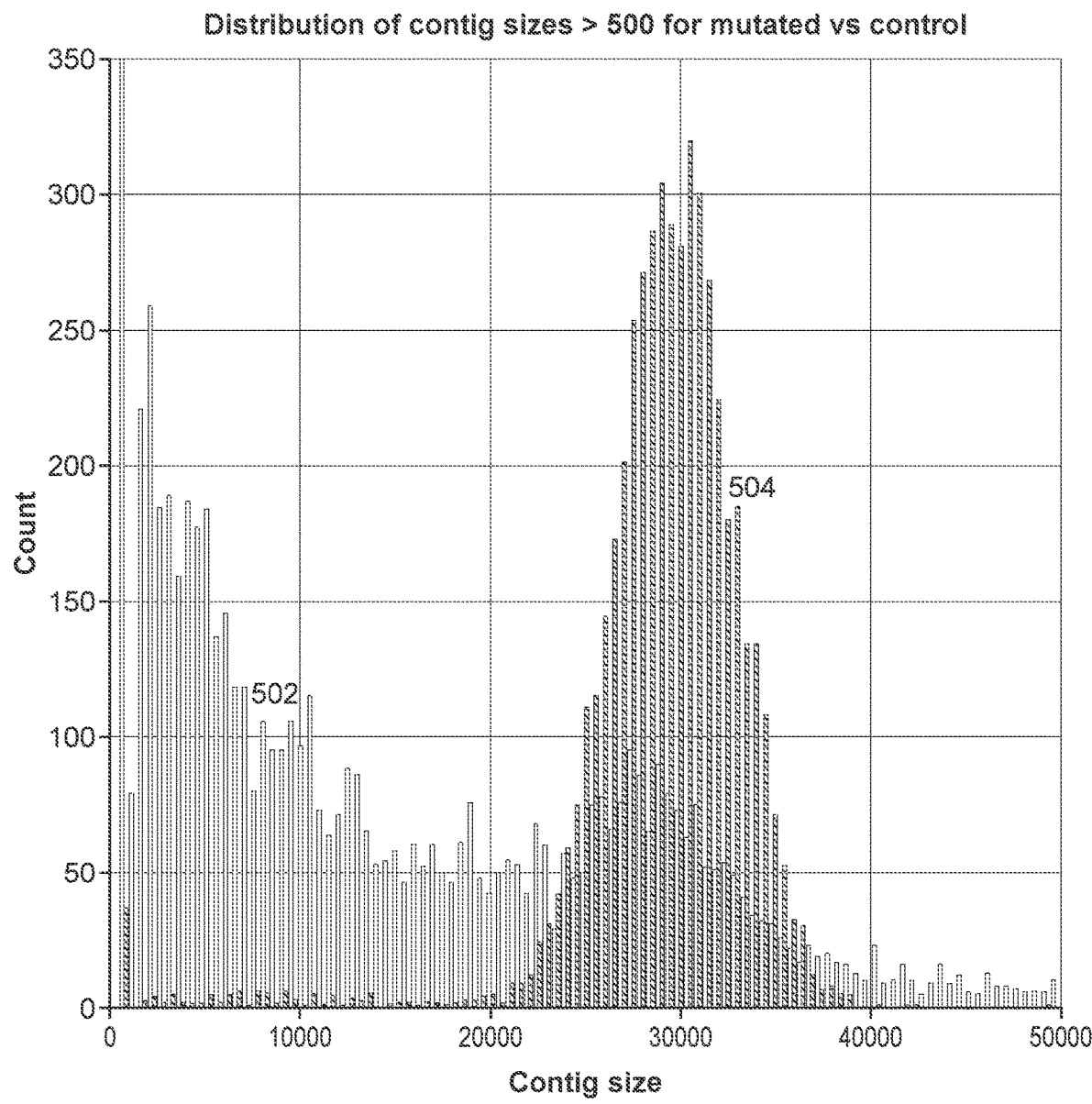
FIG. 5A illustrates contig size after assembly of mutated and non-mutated simulated sequencing reads in accordance with embodiments of the invention.

Turning to FIGS. 5A-E, the assembly of mutated reads into contigs is illustrated and contig length and mutation rate is compared to reads of other sequencing technologies. The mutated reads will assemble into contigs in accordance with many embodiments, such as illustrated in FIGS. 5A-5B. In particular, FIG. 5A illustrates assembled contigs from the non-mutated and mutated samples of certain embodiments. The dark bars 502 illustrate the count of non-mutated contigs of various sizes, which show many contigs below 10,000 base pairs and a small peak in the 20,000-30,000 base pair range. The light bars 504 illustrate the contigs of the mutated sequence that show a relatively strong distribution peaking in the 30,000 base pair range, indicating that embodiments will assemble the contigs in accordance with the sizes generated via MDA. Turning to FIGS. 5B-5E, distributions of fragment size versus error rate in accordance with a number of embodiments and sequencing platforms are illustrated. In particular, FIG. 5B illustrates the fragment size of and mismatch rates of mutated fragments generated in many embodiments, while FIG. 5C-5E illustrate read length and error rate of Pacific BioSciences (PacBio), Oxford Nanopore (Nanopore), and Illumina sequencers, respectively. As Illumina sequencers produce shorter reads with high accuracy, the distribution of read length and error rate is confined to a point very near the origin point of the graph, which is circled. As seen in these figures, many embodiments generate a tighter distribution mismatch rate for fragment length, highlighted via a box. The box in FIGS. 5C-5E illustrate the distribution generated by certain embodiments as a comparison.

Figure 6A:
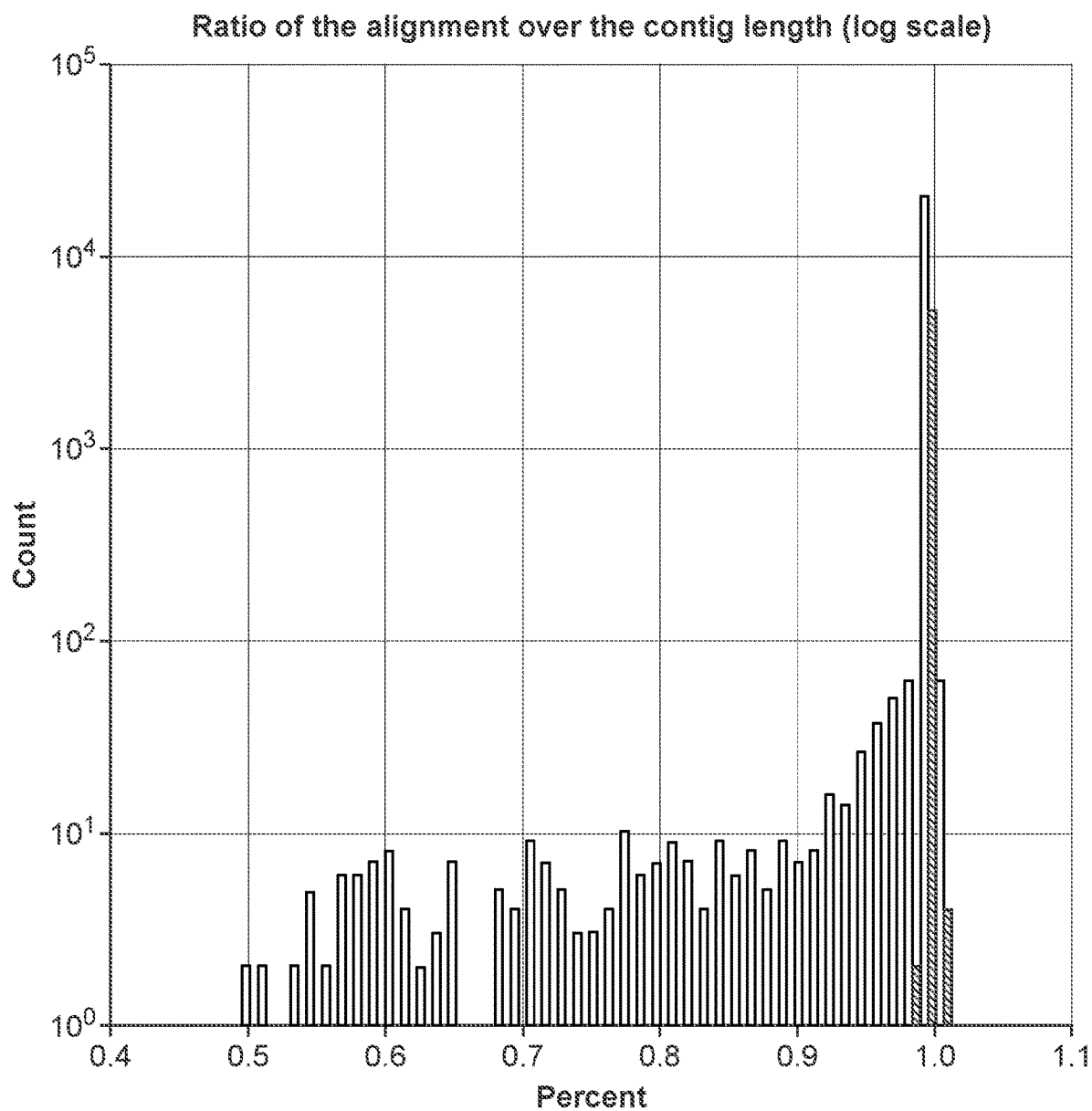
FIG. 6A illustrates the alignment ratio of contigs assembled from mutated and non-mutated simulated sequencing reads in accordance with embodiments of the invention.
Figure 6B:
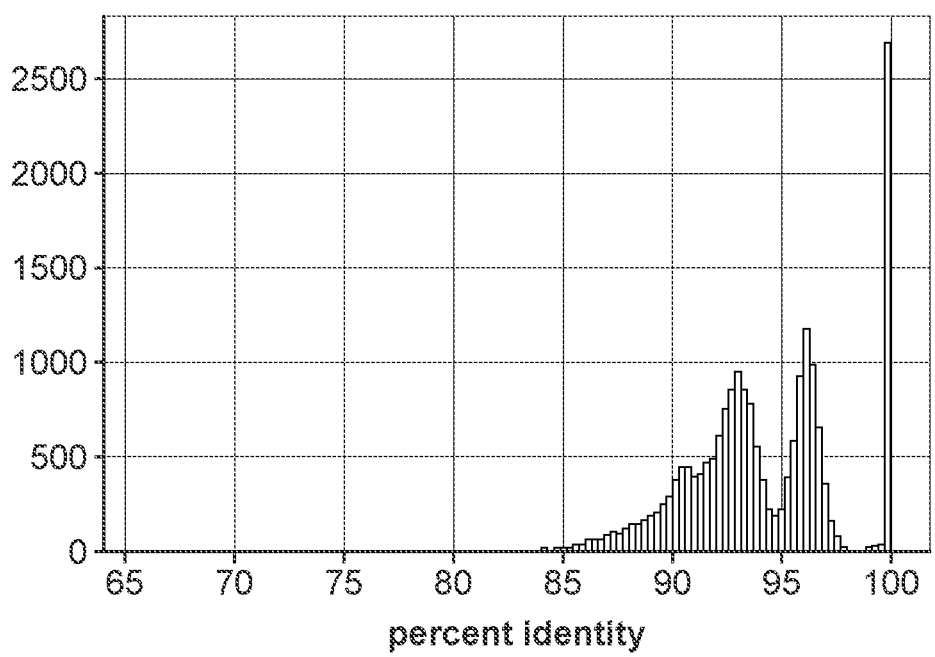
FIG. 6B illustrates alignment percent identity of contigs assembled from mutated sequencing reads in accordance with embodiments of the invention.
Figure 6C:
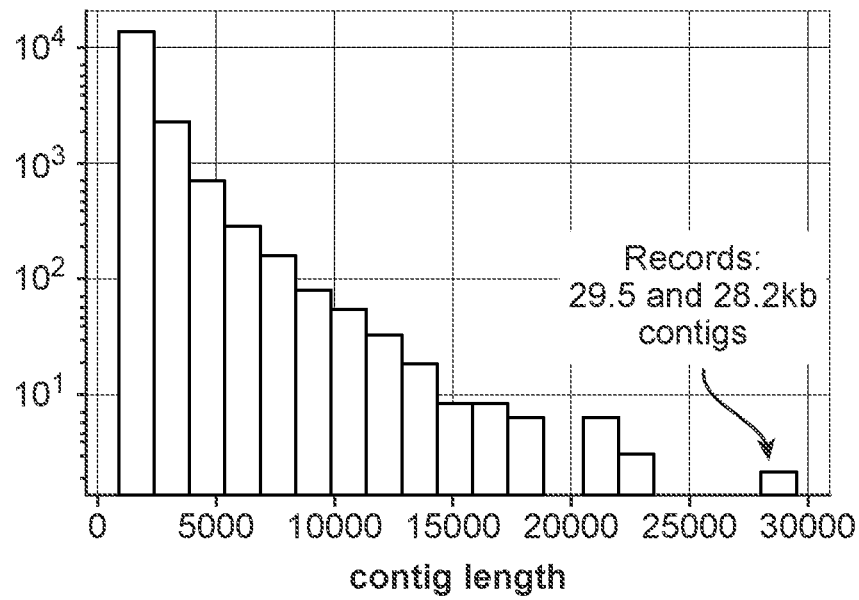
FIG. 6C illustrates contig size after assembly of mutated sequencing reads in accordance with embodiments of the invention.

Turning to FIGS. 6A-6B, the alignment rate and percent identity of contigs assembled in accordance with certain embodiments are illustrated. In particular, FIG. 6A shows a mutated sample (light) having a range of alignment from close to 1.0, indicated that very few of the mutated contigs align less than their full length. In contrast, non-mutated contigs (dark) of certain embodiments show a range of alignment from approximately 0.5 to 1.0, indicating that a number of the non-mutated contigs are likely to be misassembled. Additionally, FIG. 6B illustrates the percent identity of contigs assembled in accordance with some embodiments. As seen in FIG. 6B, assembled contigs in accordance with many embodiments show a decreased percent identity as compared to the reference sequence, such that assembled contigs in certain embodiments show a distribution of identity with three peaks, one peak is at approximately 97% identity, a second peak is at around 93% identity, and a third peak is at around 91% identity, where each peak represents multiple rounds of amplification within the certain embodiments. The peak at 100% identity indicates that non-mutated template DNA is present in a number of embodiments. Additionally, FIG. 6C illustrates the length of assembled contigs in accordance with many embodiments, to show that embodiments are capable of generating mutated contigs of approximately 30,000 base pairs.

Figure 7D:
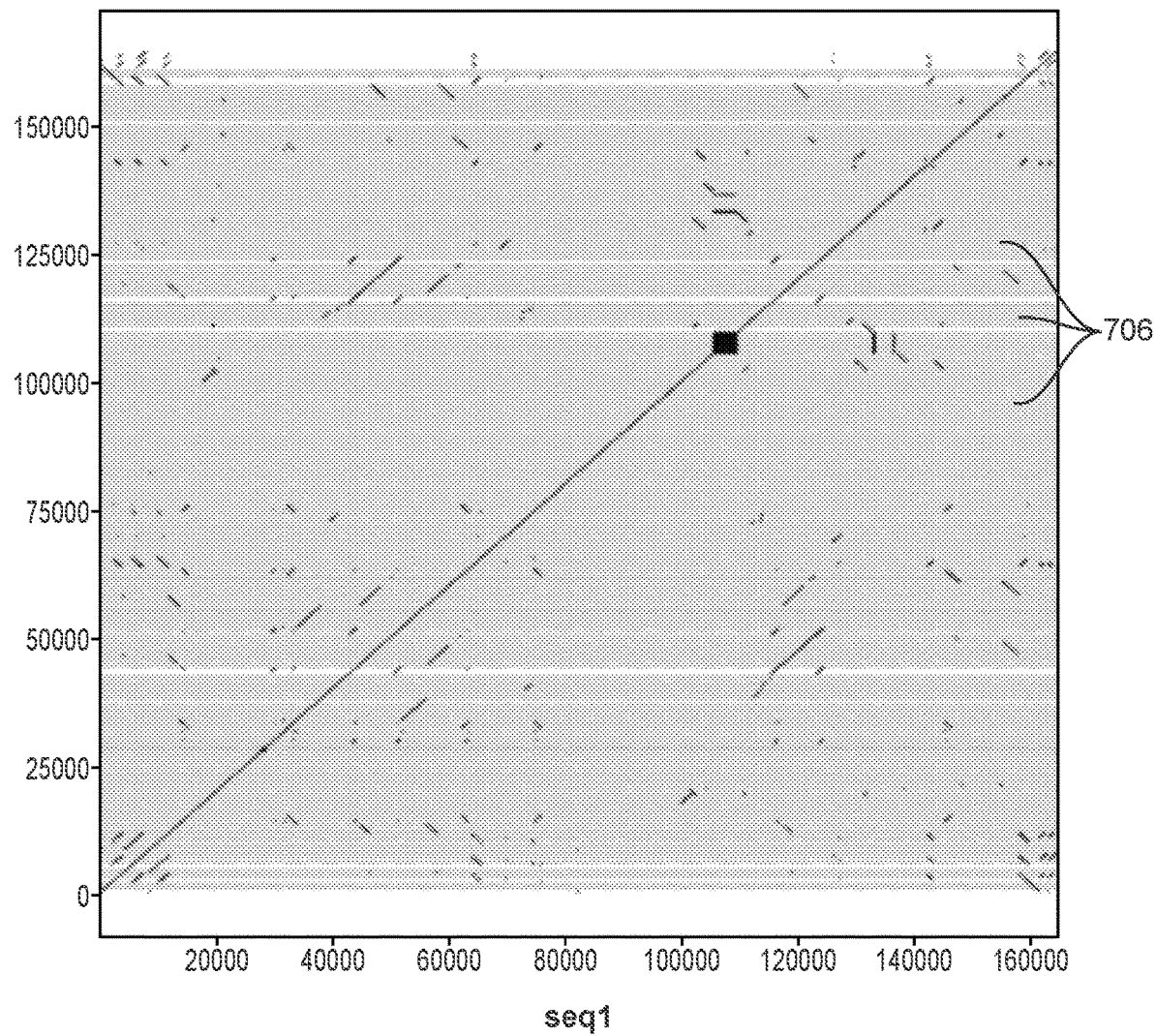
FIG. 7D illustrates a dot plot of the assembly of a repetitive bacterial artificial chromosome in accordance with embodiments of the invention.

Turning to FIGS. 7A-7D, assembly of a highly repetitive bacterial artificial chromosome (BAC) is illustrated, in accordance with many embodiments. In particular, FIG. 7A illustrates a table showing the assembly of the BAC from non-mutated reads assembled using the common short-read assemblers, SPAdes and ABySS, and the assembly of the BAC using mutated sequences and assembled in accordance with many embodiments. Specifically, FIG. 7A illustrates that embodiments are capable of assembling the BAC into a single fragment for the full 164,666 bp of the BAC. FIG. 7B graphically illustrates the assembly as the x-axis 702 having a total length of 164,666 bp. Line 704 represents the read depth coverage of the short reads coming from an Illumina sequencer. Further, blocks 706 represent contigs assembled using SPAdes assembler from non-mutated sequence that aligned the assembled BAC sequence, indicating that the non-mutated sequencing is unable to assemble the full BAC sequence. FIG. 7C illustrates a more detailed view of the BAC, showing details from the positions 0 bp to approximately 60,000 bp of the assembled sequence. As in FIG. 7B, blocks 706 represent the contigs assembled from non-mutated sequence aligned to the assembled BAC sequence, which leave gaps 708 between many of these contigs. In contrast to the non-contiguous assembly from non-mutated sequences, contigs generated from mutated sequence 710 span these gaps, showing that many embodiments are capable of assembling across genetic and/or genomic regions that current methodologies are incapable of assembling. Additionally, FIG. 7D illustrates a dot plot of the assembly against itself, which shows the ability of some embodiments to assemble highly repetitive sequences. Similar to FIGS. 7B-7C, blocks 706 in FIG. 7D identify large contigs assembled from non-mutated sequence, which do not assemble the entire length of the BAC sequence.

EXEMPLARY EMBODIMENTS

Although the following embodiments provide details on certain embodiments of the inventions, it should be understood that these are only exemplary in nature, and are not intended to limit the scope of the invention.

Example 1: Generating Mutations in Sample Nucleic Acid

Methods:

In one exemplary embodiment, genomic DNA from *Arabidopsis thaliana* was acquired and mutated using MDA. In this exemplary embodiment, 1 μL of 2× alkaline denaturation solution and 1 μL of genomic DNA (at a concentration of ~5-10 ng/μL) were added to a reaction tube, mixed gently, and incubated at room temperature for 3 minutes. After this, the reaction tube was placed on ice, where 2 μL of 2× alkaline denaturation solution was added and mixed gently. After which, 16 μL of a master mix was added and mixed gently. The master mix consisted of Phi29 DNA polymerase, polymerase buffer, bovine serum albumin (BSA), random exo-resistant hexamer primers, 100 μM dNTP mix, and 200 μM dPTP. This reaction solution was incubated at 30° C. for 3 hours and 30 minutes. The reaction was stopped by increasing the temperature of the reaction to 65° C. for 3 minutes in order to denature the polymerase, followed by a 12° C. hold until further processing. The sample was amplified by a clean MDA amplification following the same reaction conditions for mutational MDA with the exception that no dPTP was included in the clean MDA reaction solution. This was followed by size selection and dilution. Sequencing libraries were generated from the mutated sample and a non-mutated control genomic DNA sample and sequenced on an Illumina MiSeq to a length of 98 base pairs. The reads were then aligned to the *A. thaliana* reference genome sequence Results:

FIG. 3 illustrates an electropherogram of fragments produced after the clean MDA demonstrating that MDA can generate large fragments in the range of 10,000 base pairs to approximately 50,000 base pairs. Additionally, FIG. 8 illustrates the number of reads containing a specific number of base pair mismatches when aligning the sequencing libraries against the *A. thaliana* reference genome sequence. The control (i.e., non-mutated) DNA sequence 802 is illustrated in dark, where the majority of reads contained no mismatches, and very few reads contain more than 5 mismatches per read. In contrast, the mutated sequence 804, in light, illustrates a distribution of reads containing as many as 20 mismatches and an average of approximately 10 mismatches per read; at a read length of 98 bp, 10 mismatches indicate a mutation rate of approximately 10%.

Conclusion:

This exemplary embodiment shows how embodiments can reliably produce large fragments of mutated DNA with a desirable mutation frequency.

Example 2: Mutational Spectrum

Methods:

In another exemplary embodiment, the Mutational MDA was performed on *A. thaliana* DNA according the methods in Example 1 and the mutational spectrum was investigated for the purposes of distinguishing it from sequencing error and misalignment background noise. Additionally, three samples varied the concentration of dPTP in the reaction mix, such that a first sample used 200 μM dPTP, a second sample used 400 μM dPTP, and a third sample used 600 μM dPTP. Read alignments to the reference assembly were performed using the Bowtie 2 software.

Figure 13A:
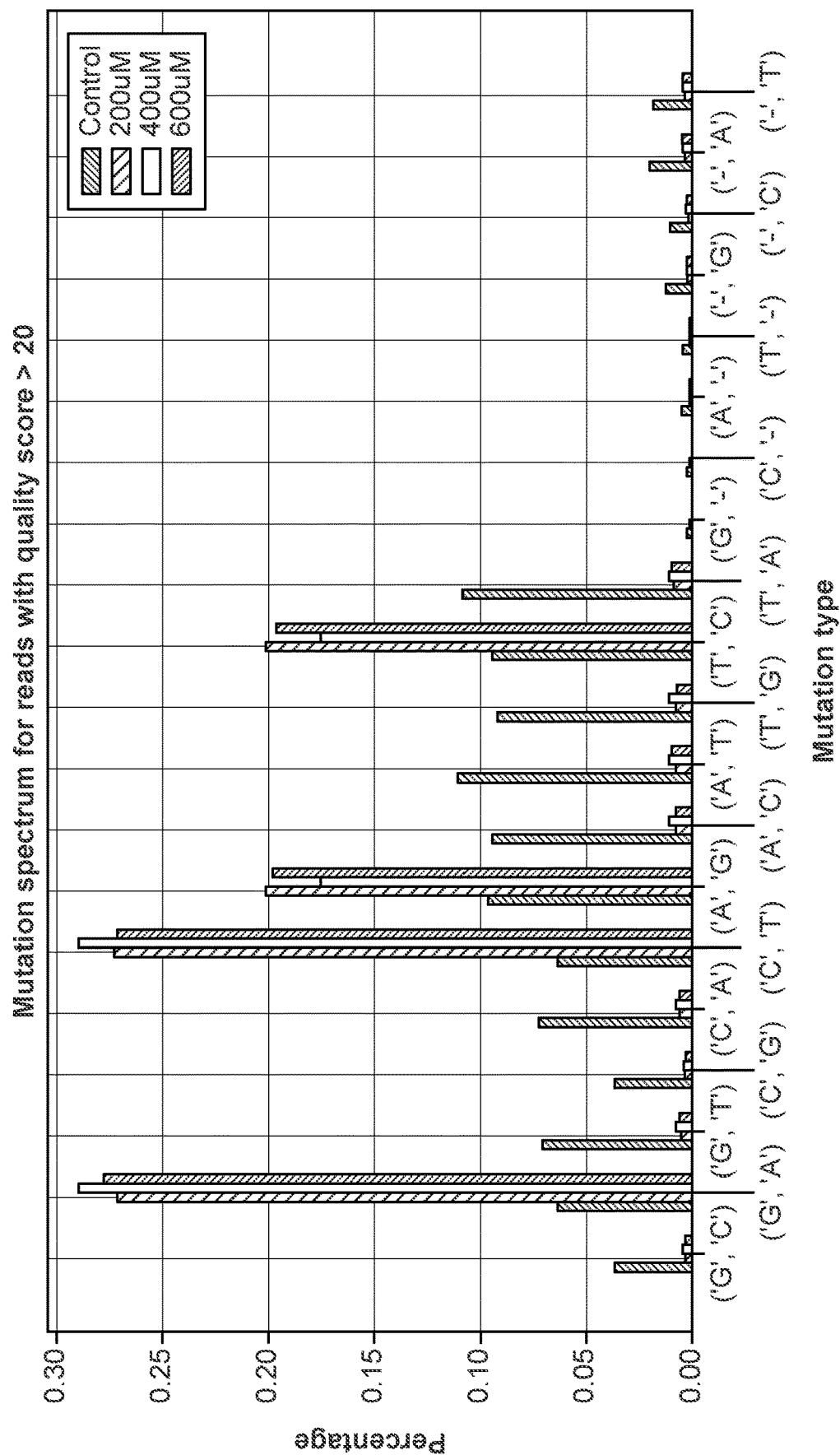
FIG. 13A illustrates the mutation type present in sequencing reads generated from a non-mutated sample and three separate mutated sequence sample sequencing reads in which the concentration of a nucleotide analog was altered in accordance with embodiments of the invention.
Figure 13B:
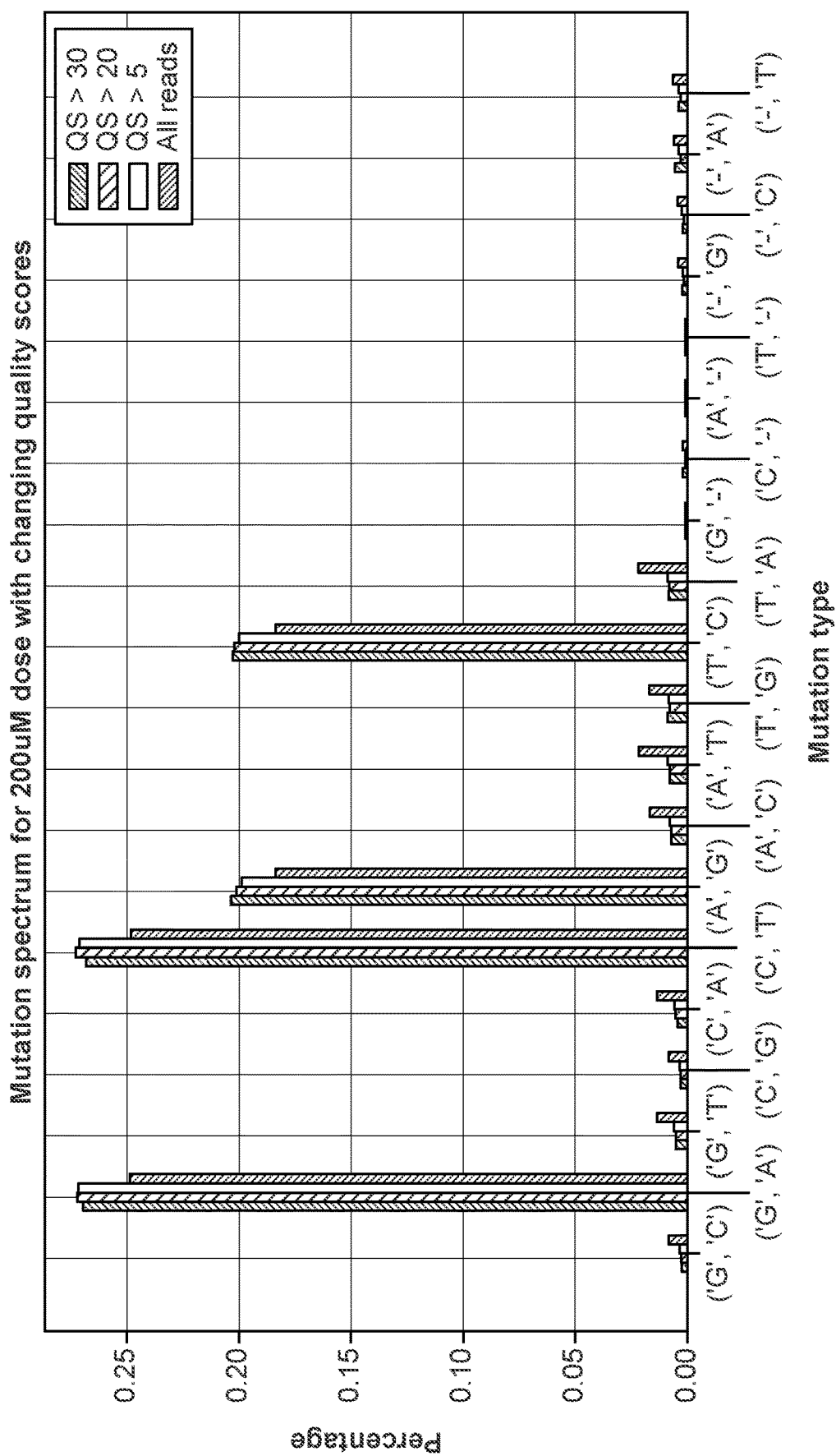
FIG. 13B illustrates the mutation type present in sequencing reads generated from a mutated sequence sample in which the sequencing reads were filtered for alignment quality in accordance with embodiments of the invention.

Results:

The mutation type generated in this embodiment is predictably purine-to-purine or pyrimidine-pyrimidine. FIG. 13A illustrates the type of mutation for aligned reads from the non-mutated (left), first (middle left), second (middle right), and third (right) samples with quality scores of at least 20. As seen in FIG. 13A, the non-mutated sample shows mutations across all types of mutations, including pyrimidine-to-purine and purine-pyrimidine, while the mutated samples show increased levels of guanine-to-adenine and adenine-to-guanine (purine-to-purine) and cytosine-to-thymine and thymine-to-cytosine (pyrimidine-to-pyrimidine) mutations. Also, when filtered for alignment quality, reads with purine-to-purine mutations and pyrimidine-to-pyrimidine mutations showed higher quality alignments. FIG. 13B illustrates the mutation types in reads from the first sample when filtered for alignment quality. Specifically, the first bars represent quality scores greater than 30; the second bars represent quality scores above 20; the third bars represent quality scores above 5; and the fourth bars represent all reads, independent of quality score. As seen in FIG. 13B, the purine-to-purine mutations and pyrimidine-to-pyrimidine mutations show higher quality alignments overall indicating that the much of the others can be attributed to poor quality alignments. For clarity, it should be noted that in FIG. 13A and FIG. 13B data is represented as a percentage of the total number of mutations.

Figure 12:
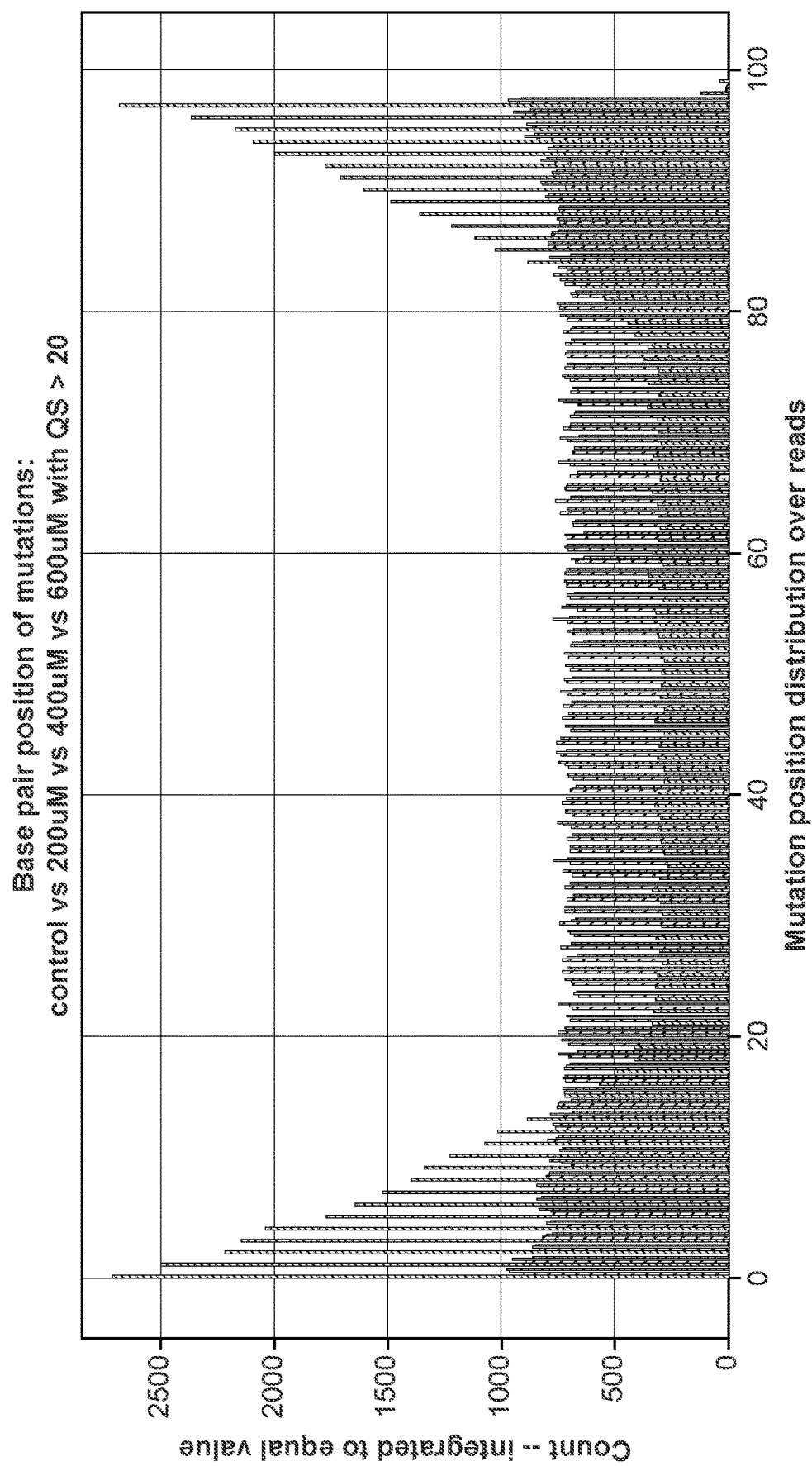
FIG. 12 illustrates the position of base pair mismatches from 98 base pair sequencing reads from a non-mutated sample and a mutated sample in accordance with embodiments of the invention.

Additionally, the position of the mutation is relatively equal across the length of a sequencing read coming from a non-control sample, as illustrated in FIG. 12. As seen in FIG. 12, the x-axis represents the length of a 98 base pair sequencing read, as used in the present embodiment, and the vertical bars represent the number of reads with a mismatch at each specific base pair in the 98 base pair reads (normalized over the entire sequence). In FIG. 12, the left most bars are control (non-mutated) sequencing reads, while the second, third, and fourth bars represent the first, second, and third mutated samples, respectively. The increased counts of reads with errors at or near the ends of the reads in the control sample are known phenomena with Illumina sequencing and are associated with sequencing errors.

Conclusion:

The presence of dPTP in the reaction generates a clear mutational spectrum relative to background sequencing and alignment error rates. Further, mutations generated by mutational MDA are evenly distributed across a sequencing read without bias toward any specific location on the read. Knowledge of this particular spectrum can aid in downstream bioinformatics and error correction.

Example 3: Assembling Mutated Fragments

Methods:

In one exemplary embodiment, the sequence of chromosome III of *Caenorhabditis elegans* was computationally mutated at a rate comparable to what can be generated by methods described above. Synthetic sequencing reads were generated based on a control (non-mutated) and a simulated mutated chromosome III sequences using the ART simulated read program. These simulated mutated sequences were selected by sampling the chromosome randomly with a window centered around 30,000 bp (with a 3,000 bp standard deviation) for a total of 0.5× coverage. The control and mutated sequencing reads were assembled using the ABySS assembler to recreate large fragments. The assembled contigs were then aligned to the chromosome III reference sequence. Finally, this process was repeated 21 times, generating mutated and non-mutated assembled contigs for a total of 10.5× coverage. These assembled contigs were subsequently assembled into a final assembly using the Canu assembler.

Results: The size of assembled contigs from the non-mutated and mutated samples is illustrated in FIG. 5A. In FIG. 5A, dark bars 502 illustrate the count of non-mutated contigs of various sizes, which show many contigs below 10,000 base pairs and small peak in the 20,000-30,000 base pair range. The light bars 504 illustrate the contigs of the mutated sequence that show a relatively strong distribution peaking in the 30,000 base pair range.

Further, FIG. 6A illustrates the rate of the alignment of the contigs to the reference sequence. As seen in FIG. 6A, the non-mutated sample (dark) shows a range of alignment from approximately 0.5 to 1.0, showing that a large number of non-mutated contigs align less than their full length, showing that the non-mutated sequences are likely misassembled. In contrast, the mutated contigs (light) show a range of alignment close to 1.0, indicating that the introduction of mutations facilitates proper assembly and lowers the rate of misassembly.

Figure 9A:
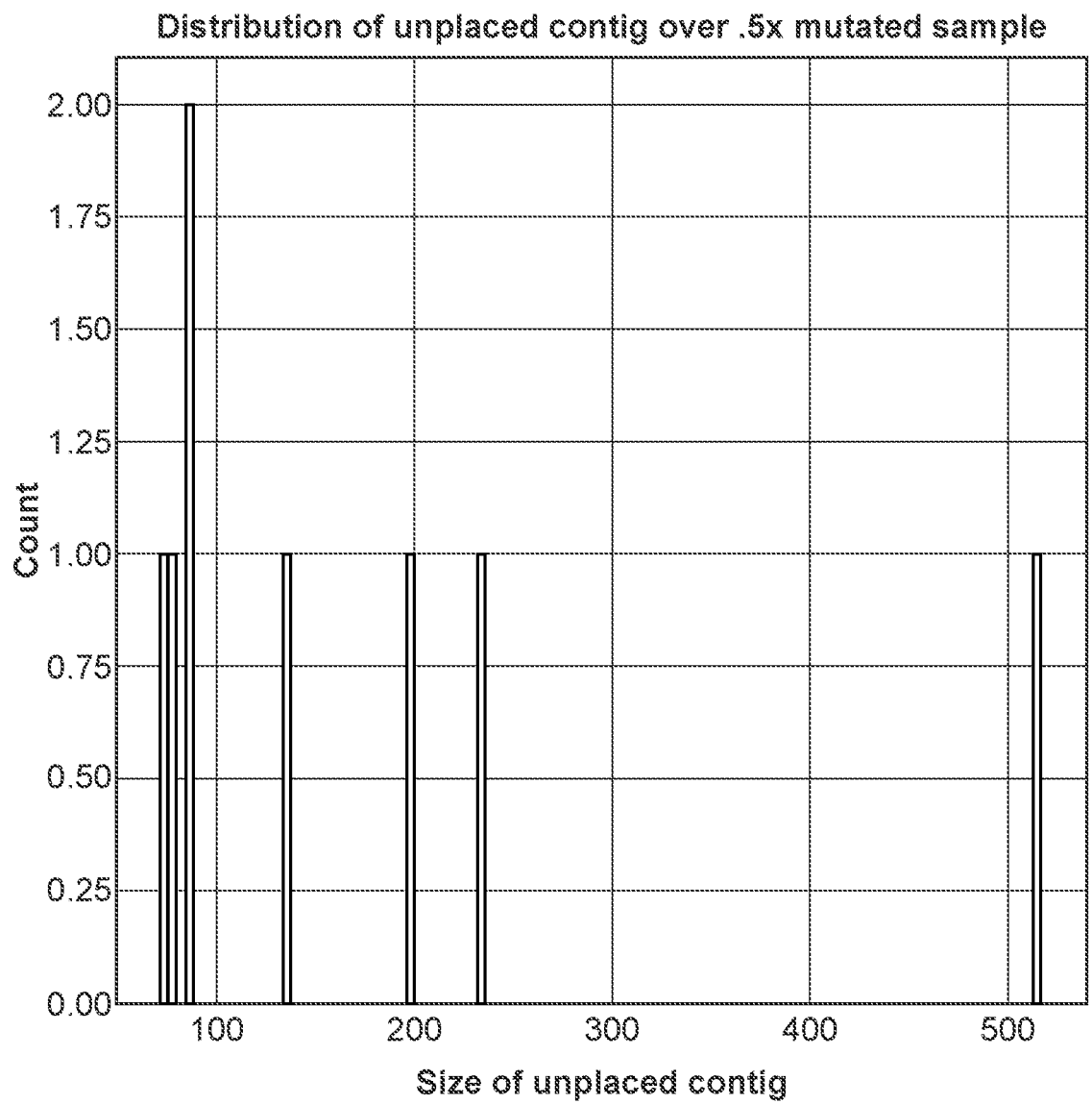
FIG. 9A illustrates the number of assembled contigs from a simulated mutated assembly that did not map to a reference sequence in accordance with embodiments of the invention.
Figure 9B:
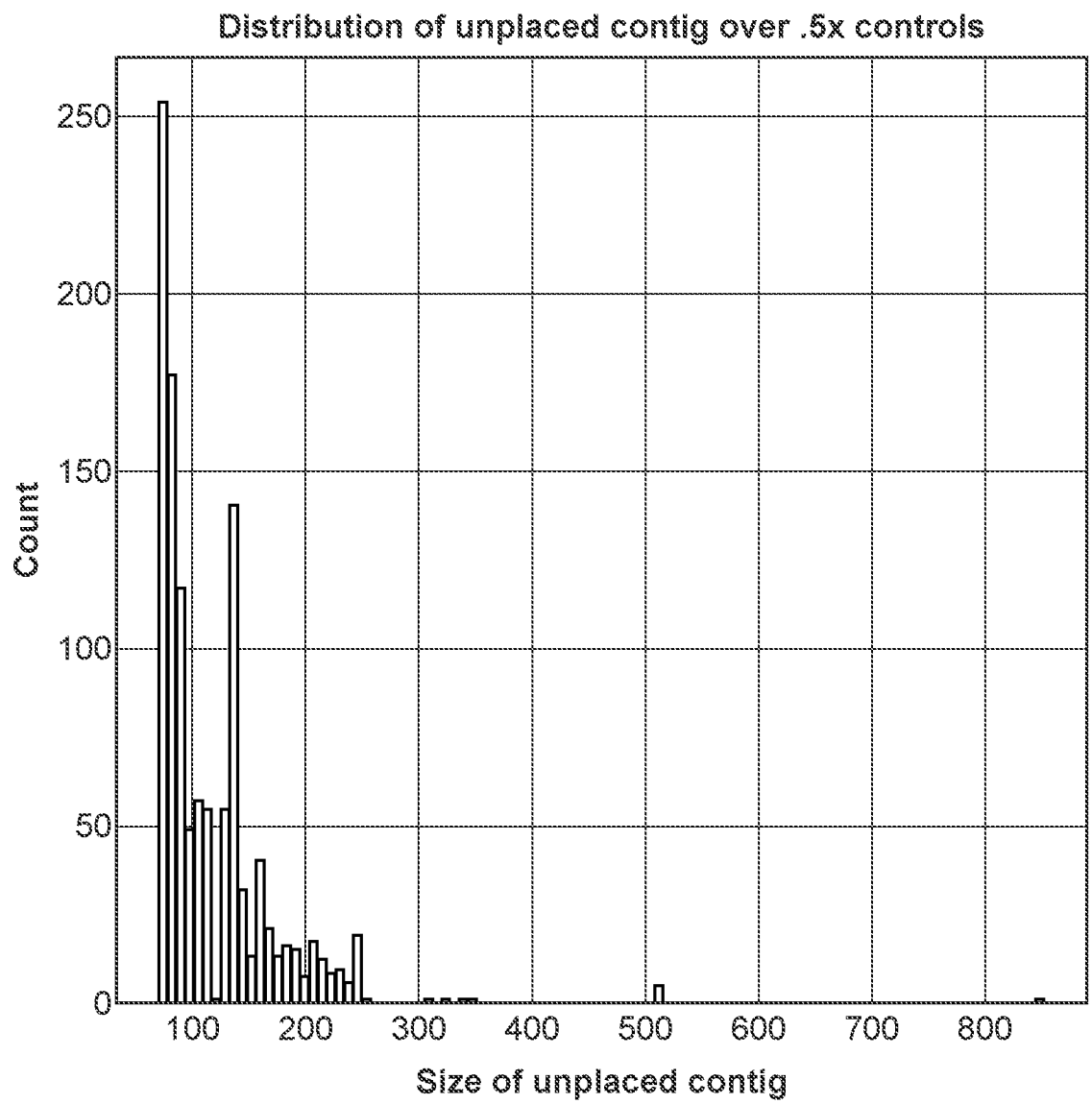
FIG. 9B illustrates the number of assembled contigs from a simulated non-mutated assembly that did not map to a reference sequence in accordance with embodiments of the invention.

Also, very few contigs do not map to the reference sequence, indicating few complete misassemblies. Out of a total of 5,209 contigs generated from the mutated sample, only 8 contigs did not align. These non-mapping contigs are illustrated in FIG. 9A. As seen in FIG. 9A, most of the non-mapping contigs below 500 base pairs in size, while only one contig was above 500 base pairs. In contrast, the non-mutated sample generated 22,221 contigs, of which 1,144 did not map, as shown in FIG. 9B. Like in the mutated sample, the majority of the non-mapping contigs were below 500 base pairs in size.

Figure 10A:
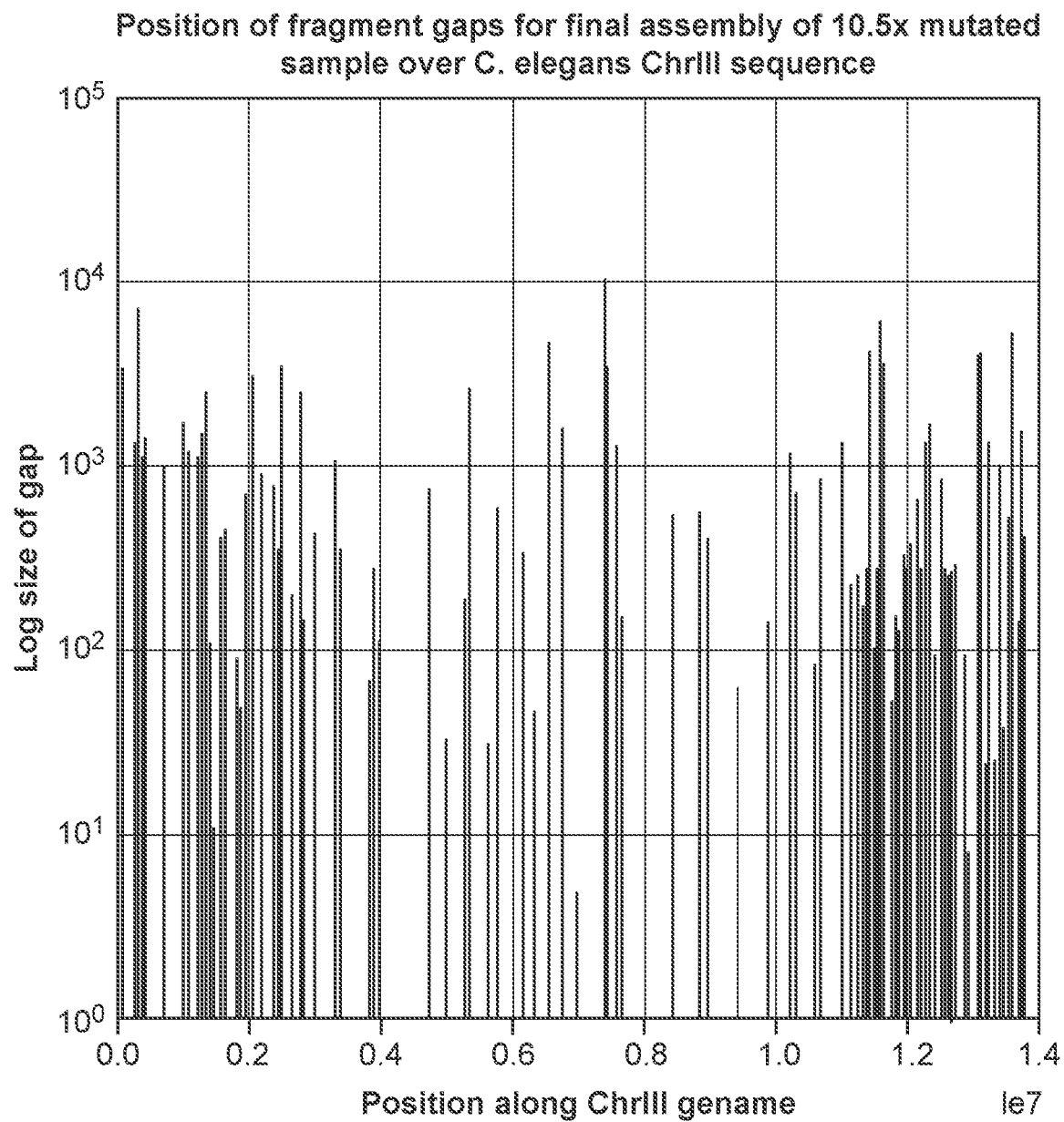
FIG. 10A illustrates gap positions in a reference sequence when assembled contigs from a simulated non-mutated assembly were mapped to the reference sequence in accordance with embodiments of the invention.
Figure 10B:
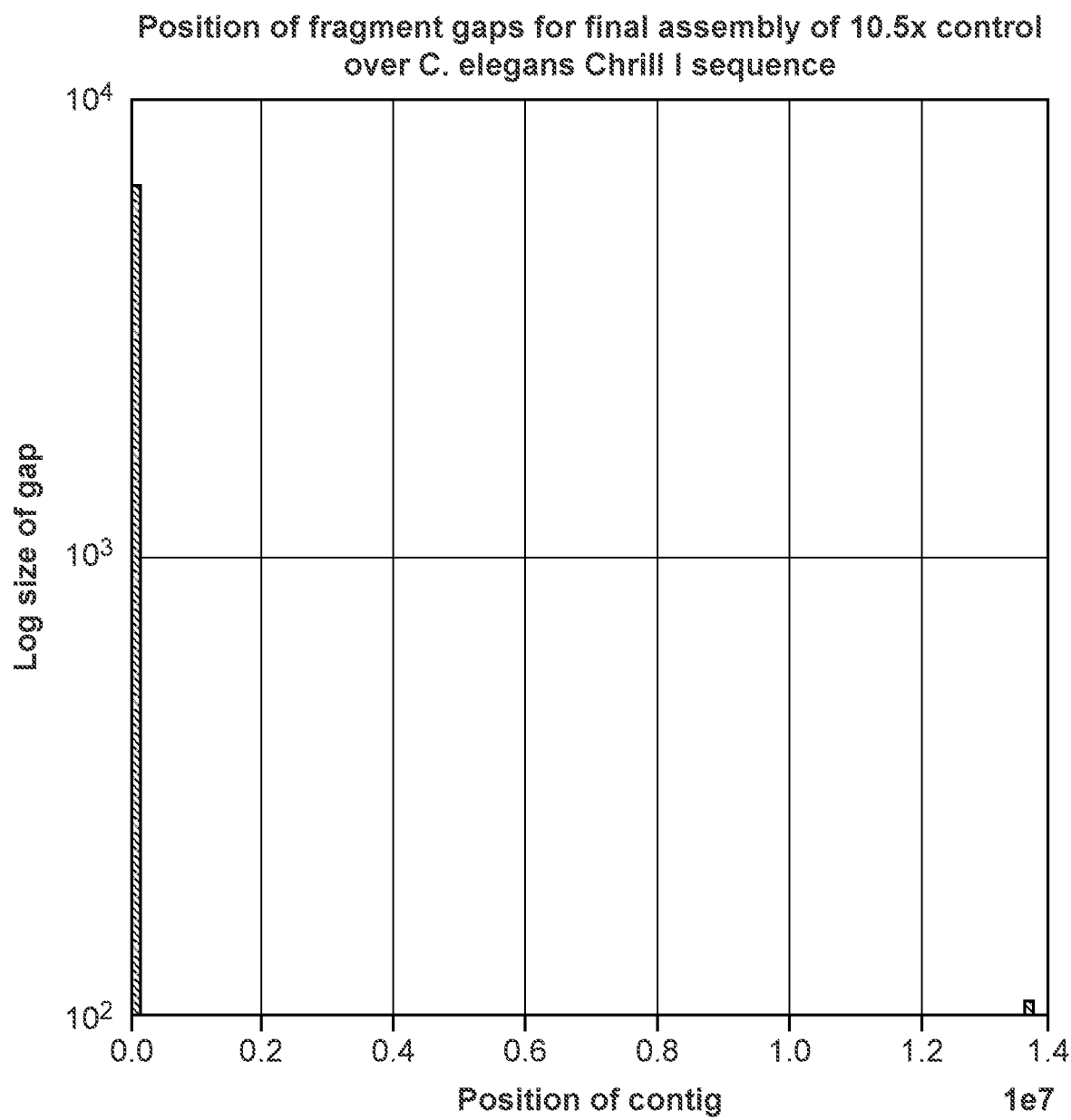
FIG. 10B illustrates gap positions in a reference sequence when assembled contigs from a simulated mutated assembly were mapped to the reference sequence in accordance with embodiments of the invention.

Additionally, the final assembly of the control showed numerous gaps in the genome, as illustrated in FIG. 10A, where the vertical bars demonstrate gap sizes at specific locations along the length of chromosome III. In contrast to this, the final assembly of the mutated contigs produced gaps at only the distal ends of the chromosomes, as illustrated in FIG. 10B.

Figure 11A:
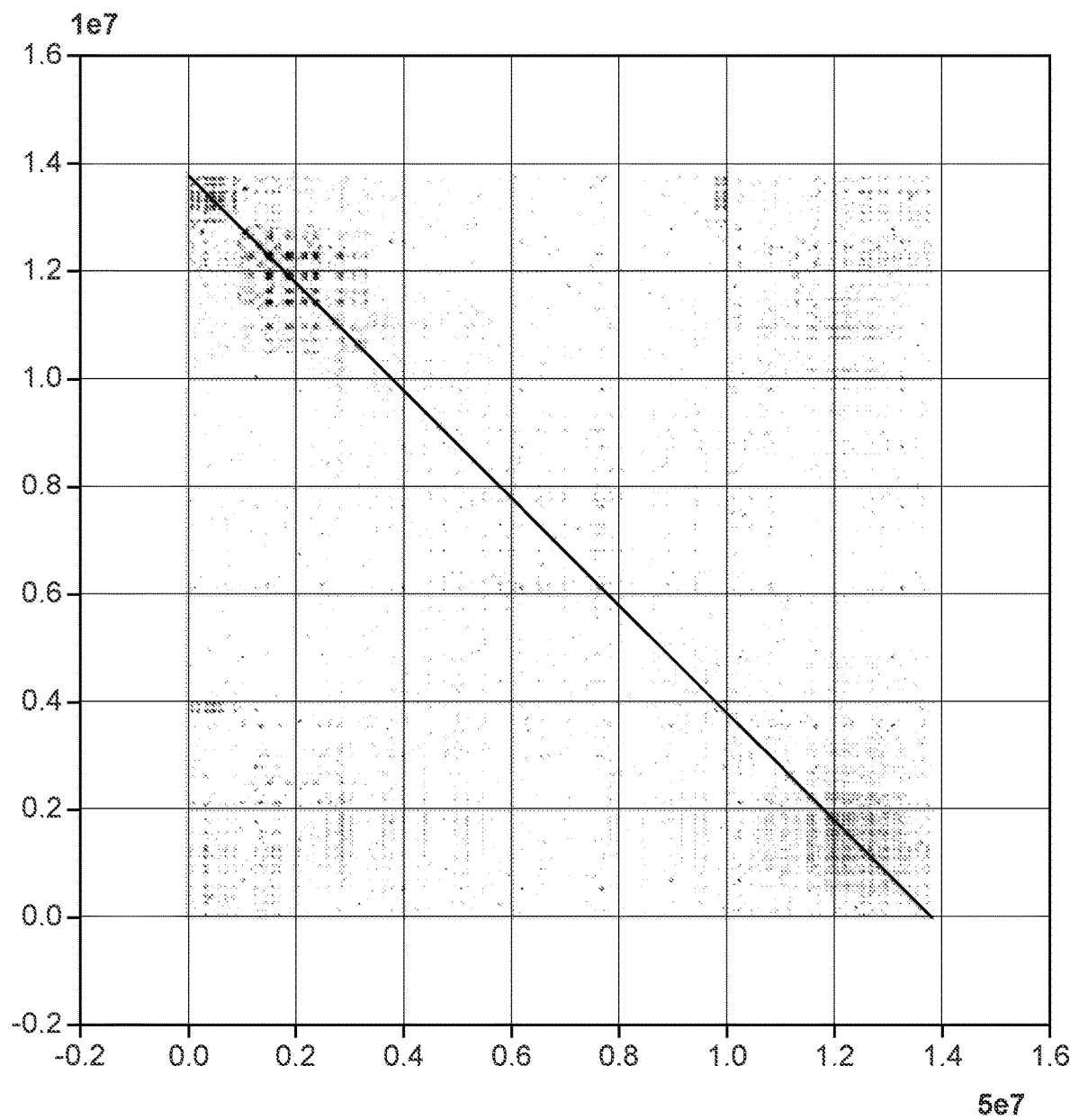
FIG. 11A illustrates a dot plot of an assembled *Caenorhabditis elegans* Chromosome III from a mutated sample against the reference sequence of Chromosome III in accordance with embodiments of the invention.
Figure 11B:
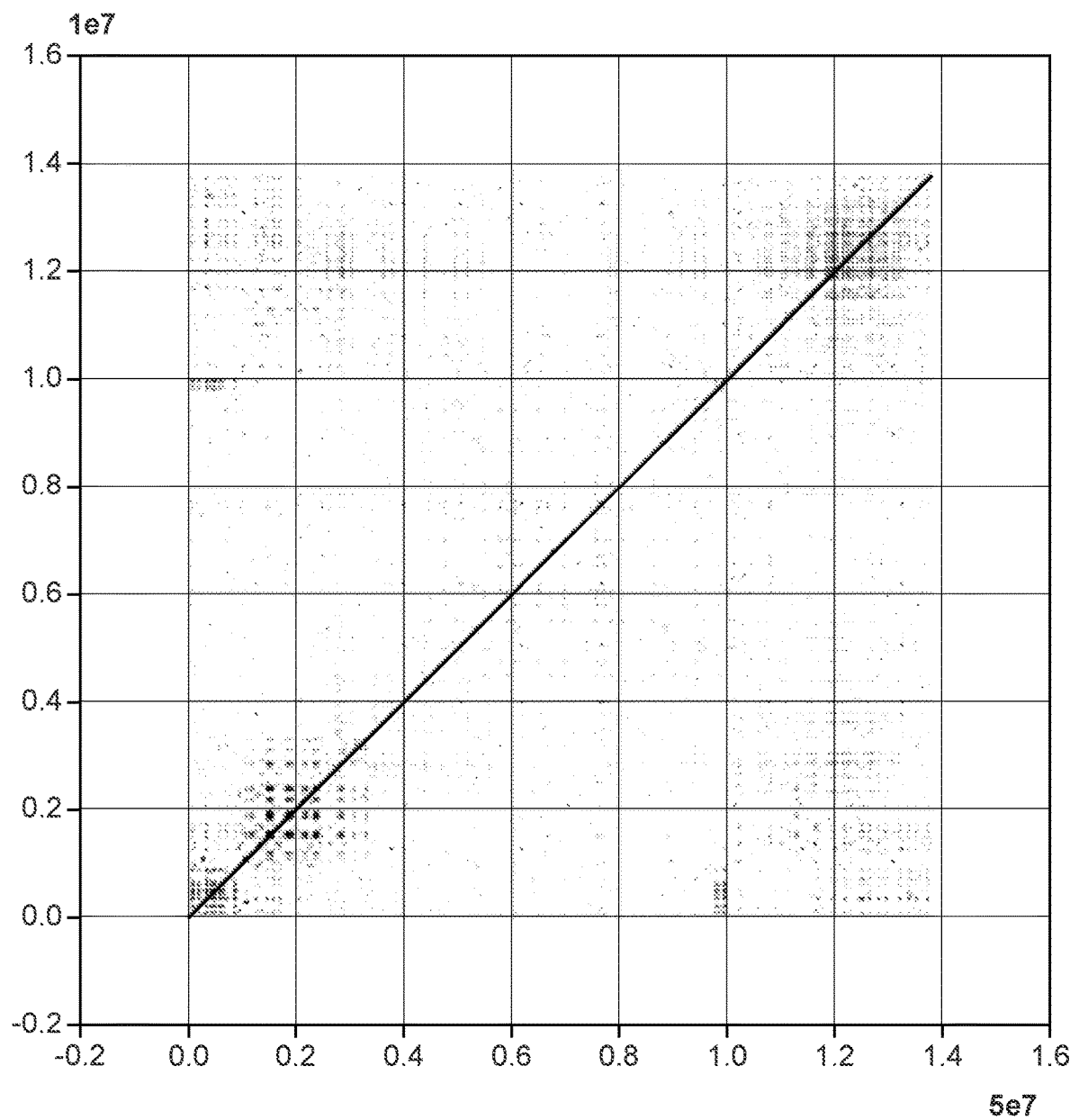
FIG. 11B illustrates a dot plot of the reference sequence of *Caenorhabditis elegans* Chromosome III against itself in accordance with embodiments of the invention.

The final assembly of the mutated contigs shows significant homology with the reference chromosome III sequence, as illustrated in FIG. 11A. FIG. 11A illustrates a dot-plot of homology between two sequences, where the long diagonal extending from the upper left to the lower right of the plot shows significant homology and uniformity between the mutated assembly (y-axis) and the reference sequence (x-axis). The off-diagonal marks indicate regions of repetitive DNA, where the sequence exists at multiple locations along the chromosome. This figure shows incredible similarities to the comparison of the reference chromosome III sequence to itself, as illustrated in FIG. 11B. In FIG. 11A, the long diagonal extends from the upper left to the lower right, indicating that the mutated assembly represents the complementary sequence to the reference sequence.

Conclusion:

Mutated sequence produces larger contigs with lower misassembly rates that subsequently assemble into a final assembly that cover more of the genome with far fewer gaps and with a high level of fidelity to the sequence from which it originates. Thus, mutating a sample prior to sequencing provides a better assembly than non-mutated samples.

Example 4: Assembling a Repetitive BAC Sequence

Methods:

In another exemplary embodiment, a repetitive bacterial artificial chromosome (BAC) was assembled. In this embodiment, BAC 2-5C-13-12 from a maize (*Zea mays*) was isolated, mutated, sequenced, and assembled using a combination of SPAdes, ABySS, and Canu assemblers in accordance with the methods described herein. A control sample (non-mutated) was separately sequenced and assembled using SPAdes and ABySS assemblers.

Results:

FIG. 7A illustrates a table showing the results of the non-mutated SPAdes and ABySS assembly as well as the mutated assembly. As seen in FIG. 7A, the mutated assembly resulted in a single contig of 164,666 bp in length with no gaps, whereas the non-mutated control samples resulted in 33 or 44 contigs, thus lacking the ability to fully assemble the BAC sequences.

FIG. 7B graphically illustrates the assembly as the x-axis 702 having a total length of 164,666 bp. Line 704 represents the read depth coverage of the short reads of the control sample coming from an Illumina sequencer. Further, blocks 706 represent contigs assembled using SPAdes assembler from non-mutated sequence that aligned the assembled BAC sequence, indicating that the non-mutated sequencing is unable to assemble the full BAC sequence.

FIG. 7C illustrates a more detailed view of the BAC, showing details from the positions 0 bp to approximately 60,000 bp of the assembled sequence. As in FIG. 7B, blocks 706 represent the contigs assembled from non-mutated sequence aligned to the assembled BAC sequence, which leave gaps 708 between many of these contigs. In contrast to the non-contiguous assembly from non-mutated sequences, contigs generated from mutated sequence 710 span these gaps, showing that many embodiments are capable of assembling across genetic and/or genomic regions that current methodologies are incapable of assembling.

Additionally, FIG. 7D illustrates a dot plot of the assembly against itself, which shows the ability of some embodiments to assemble highly repetitive sequences. Similar to FIGS. 7B-7C, blocks 706 in FIG. 7D identify large contigs assembled from non-mutated sequence, which do not assemble the entire length of the BAC sequence.

CONCLUSION

Introducing mutations into repetitive sequences allows for the assembly of larger fragments of a genome (e.g., chromosome, subregion, etc.) without gaps.

DOCTRINE OF EQUIVALENTS

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A method comprising:
    obtaining a sample comprising a template nucleic acid;
    introducing mutations into the sample via a multiple strand displacement amplification of the template nucleic acid to create a mutated sample, wherein the amplification comprises contacting the template nucleic acid with a polymerase under conditions that promote the multiple strand displacement amplification of the template nucleic acid;
    sequencing the amplified nucleic acids comprising the mutated sample; and
    assembling the sequences of the amplified nucleic acids comprising the mutated sample to build a genome or genomic region sequence;
    wherein the polymerase is Phi29 DNA polymerase or EquiPhi29; and
    wherein introducing mutations into the sample comprises incorporating 2'-Deoxy-P-nucleoside-5'-Triphosphate (dPTP) during the amplification;
    wherein introducing the mutations with the polymerase and the dPTP facilitates the assembly and lowers the rate of misassembly.

2. The method of claim 1, further comprising:
    performing size selection on the amplified nucleic acids comprising the mutated sample to select a desired size of fragments; and
    generating a sequencing library for the size selected amplified nucleic acids.

3. The method of claim 2, further comprising:
    quantifying the size selected amplified nucleic acids; and
    changing the concentration of the size selected amplified nucleic acids to a desired concentration.

4. The method of claim 3, wherein the changing the concentration step comprises diluting the size selected amplified nucleic acids.

5. The method of claim 2, further comprising amplifying the size selected amplified nucleic acids to generate additional copies of the size selected amplified nucleic acids.

6. The method of claim 1, wherein the multiple strand displacement amplification reaction comprises utilizing Phi29 DNA polymerase.

7. The method of claim 1, wherein the amplifying step comprises utilizing approximately 0.5-10 ng of input nucleic acid.

8. The method of claim 1, wherein the multiple strand displacement amplification reaction comprises utilizing EquiPhi29.

9. The method of claim 2, wherein the generating a sequencing library step generates a sequencing library for an Illumina sequencing platform, and the sequencing step comprises utilizing an Illumina sequencing platform to sequence the nucleic acid sample.

10. A method for producing a sequencing library, comprising:
    obtaining a sample comprising a template nucleic acid;
    introducing mutations into the sample via a multiple strand displacement amplification of the template nucleic acid to create a mutated sample, wherein the amplification comprises contacting the template nucleic acid with a polymerase under conditions that promote the multiple strand displacement amplification of the template nucleic acid; and
    generating a sequencing library from the amplified nucleic acids comprising the mutated sample;
    wherein the polymerase is Phi29 DNA polymerase or EquiPhi29; and
    wherein introducing mutations into the sample comprises incorporating 2'-Deoxy-P-nucleoside-5'-Triphosphate (dPTP) during the amplification;
    wherein introducing the mutations with the polymerase and the dPTP facilitates the assembly and lowers the rate of misassembly.

11. The method of claim 10, wherein the multiple strand displacement reaction comprises utilizing Phi29 DNA polymerase.

12. The method of claim 10, wherein the multiple strand displacement amplification comprises utilizing EquiPhi29.

13. The method of claim 10, further comprising:
    size selecting the amplified nucleic acids; and
    quantifying the size selected amplified nucleic acids.

* * * * *